(12) United States Patent
Voolstra et al.

(10) Patent No.: US 10,376,498 B2
(45) Date of Patent: Aug. 13, 2019

(54) 3-ALKYL PYRIDINIUM COMPOUND FROM RED SEA SPONGE WITH POTENT ANTIVIRAL ACTIVITY

(71) Applicant: KING ABDULLAH UNIVERSITY OF SCIENCE AND TECHNOLOGY, Thuwal (SA)

(72) Inventors: Christian R. Voolstra, Thuwal (SA); Aubrie O'Rourke, Thuwal (SA); Stephan Kremb, Thuwal (SA)

(73) Assignee: King Abdullah University of Science and Technology, Thuwal (SA)

( * ) Notice: Subject to any disclaimer, the term of this patent is extended or adjusted under 35 U.S.C. 154(b) by 0 days.

(21) Appl. No.: 15/520,811

(22) PCT Filed: Oct. 29, 2015

(86) PCT No.: PCT/IB2015/002187
§ 371 (c)(1),
(2) Date: Apr. 20, 2017

(87) PCT Pub. No.: WO2016/067099
PCT Pub. Date: May 6, 2016

(65) Prior Publication Data
US 2018/0000799 A1    Jan. 4, 2018

Related U.S. Application Data

(60) Provisional application No. 62/072,292, filed on Oct. 29, 2014.

(51) Int. Cl.
*A61K 31/439*  (2006.01)
*A61K 31/4375* (2006.01)
*A61K 35/655*  (2015.01)

(52) U.S. Cl.
CPC ........ *A61K 31/439* (2013.01); *A61K 31/4375* (2013.01); *A61K 35/655* (2015.01);
(Continued)

(58) Field of Classification Search
None
See application file for complete search history.

(56) References Cited

U.S. PATENT DOCUMENTS 7,491,794 B2    2/2009  Blatt et al.
7,977,342 B2    7/2011  Simmen et al.
(Continued)

FOREIGN PATENT DOCUMENTS

JP    2008/214268 A    9/2008
JP    2008214268       *  9/2008
(Continued)

OTHER PUBLICATIONS

Ikeda et al., International Journal of Molecular Medicine 28: 595-598, 2011 (Year: 2011).*

(Continued)

*Primary Examiner* — Karl J Puttlitz
(74) *Attorney, Agent, or Firm* — Pabst Patent Group LLP

(57) ABSTRACT

Method for treating a viral infection in a patient, comprising administering to the patient a therapeutically effective amount of a compound, or a pharmaceutically acceptable salt thereof, comprising a moiety represented by figure (I), wherein $R_1$ is a saturated or unsaturated bivalent hydrocarbon group. Viruses subject to treatment can include HIV and flaviviruses such as west nile, dengue, or hepatitis C virus. Compositions and methods of isolation and purification are also described including from the Red Sea sponge.

(Continued)

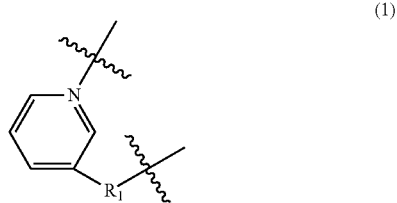

(1)

8 Claims, 10 Drawing Sheets

(52) U.S. Cl.
CPC ........... *Y02A 50/385* (2018.01); *Y02A 50/387* (2018.01); *Y02A 50/393* (2018.01)

(56) References Cited

U.S. PATENT DOCUMENTS

| | | | |
|---|---|---|---|
| 8,030,318 | B2 | 10/2011 | Simmen et al. |
| 8,097,728 | B2 | 1/2012 | Gu et al. |
| 8,778,876 | B2 | 7/2014 | Watowich et al. |
| 2002/0187999 | A1 | 12/2002 | Mayer et al. |
| 2005/0159400 | A1 | 7/2005 | Hamann et al. |
| 2010/0179186 | A1* | 7/2010 | Papke .................... A61K 31/03 514/308 |

FOREIGN PATENT DOCUMENTS

| | | |
|---|---|---|
| WO | WO 2005/084157 | 9/2005 |
| WO | WO 2006/039721 | 4/2006 |
| WO | 2007128059 | 11/2007 |
| WO | WO 2007/133614 | 11/2007 |

OTHER PUBLICATIONS

Machine Translation of JP 2008214268 retrieved from the internet at https://patents.google.com/patent/JP2008214268A/en?oq=JP+2008214268 on Jun. 27, 2018 (Year: 2008).*
International Search Report and Written Opinion received in connection with international application No. PCT/IB2015/002187; dated Feb. 26, 2016.
Albrizio, et al., (1995). "Amphitoxin, a New High-Molecular-Weight Antifeedant Pyridinium Salt from the Caribbean Sponge *Amphimedon compressa*." Journal of Natural Products 58(5): 647-652.
Arai, et al., (2009). "Haliclonacyclamines, tetracyclic alkylpiperidine alkaloids, as anti-dormant mycobacterial substances from a marine sponge of *haliclona* sp." Chem Pharm Bull (Tokyo) 57(10) 1136-1138.
Bugni, et al., (2008). "Fractionated marine invertebrate extract libraries for drug discovery." Molecules 13(6): 1372-1383.
Cregar-Hernandez et al., "Small molecule pan-dengue and West Nile virus NS3 protease inhibitors". Antivir Chem Chemother 2011, 21 (5), 209-18.
Cutignano, et al., (2004). "Polyketide origin of 3-alkylpyridines in the marine mollusc *Haminoea orbignyana*." Tetrahedron Letters 45(12): 2627-2629.
Damodaran, V., et al., (2013). "Cyclic 3-Alkyl Pyridinium Alkaloid Monomers from a New Zealand *haliclona* sp. Marine Sponge." Journal of Natural Products 76(10): 1997-2001.
Dasari et al., "Novel Pyridinium compound from marine actinomycete, *Amycolatopsis alba* var. nov DVR D4 showing antimicrobial and cytotoxic activities in vitro". Microbiological Research 2012, 167, (6), 346-351.

Davies-Coleman, et al., (1993). "A New EGF-Active Polymeric Pyridinium Alkaloid from the Sponge *Callyspongia-fibrosa*." Journal of Organic Chemistry, 58(22): 5925-5930.
Defant, A., et al., (2011). "New Structural Insights into Saraines A, B, and C, Macrocyclic Alkaloids from the Mediterranean Sponge *Reniera* (*Haliclona*) *sarai*." European Journal of Organic Chemistry (20-21): 3761-3767.
De Oliveira, et al., "Antimicrobial and antimycobacterial activity of cyclostellettamine alkaloids from sponge *pachychalina* sp.", Marine Drugs, 2006, 4 (1), 1-8.
De Oliveira, et al., "Ingenamine G and cyclostellettamines G-I, K, and L from the new Brazilian species of marine sponge *pachychalina* sp.", J Nat Prod 2004, 67 (10), 1685-9.
Evans et al., "Quantitative interpretation of diffusion-ordered NMR spectra: can we rationalize small molecule diffusion coefficients?" Angew Chem Int Ed Engl 2013, 52 (11), 3199-202.
Fujimoto et al., "Inhibition of Both Protease and Helicase Activities of Hepatitis C Virus NS3 by an Ethyl Acetate Extract of Marine Sponge *amphimedon* sp", PLOS ONE, vol. 7(11), (Nov. 7, 2011), pp. e48685.
Gil et al., Tetrahedron Letters, 36, 12, 2059-2062, 1995.
Hirano, et al., (2000) "Pyrinodemins B-D, potent cytotoxic bis-pyridine alkaloids from marine sponge *amphimedon* sp." Chemical & Pharmaceutical Bulletin 48(7): 974-977.
Jimenez, et al., (2000). "Upenamide: An unprecedented macrocyclic alkaloid from the Indonesian sponge *echinochalina* sp." Journal of Organic Chemistry 65(25): 8465-8469.
Kariya, et al., (2006). "Pyrinadines B-G, new bis-pyridine alkaloids with an azoxy moiety from sponge *cribrochalina* sp." Bioorganic & Medicinal Chemistry 14(24): 8415-8419.
Kariya, et al., (2006). "Pyrinadine A, a novel pyridine alkaloid with an azoxy moiety from sponge *cribrochalina* sp." Tetrahedron Letters 47(6): 997-998.
Kobayashi, et al., (1990). "Niphatesines a-D, New Antineoplastic Pyridine Alkaloids from the Okinawan Marine Sponge *niphates* Sp." Journal of the Chemical Society-Perkin Transactions 1(12): 3301-3303.
Kobayashi, et al., (1989). "Theonelladins-a-D, Novel Antineoplastic Pyridine Alkaloids from the Okinawan Marine Sponge *Theonella-swinhoei*." Tetrahedron Letters 30(36): 4833-4836.
Kobayashi, et al., (1994). "Keramaphidin-B, a Novel Pentacyclic Alkaloid from a Marine Sponge *amphimedon* Sp—a Plausible Biogenetic Precursor of Manzamine Alkaloids." Tetrahedron Letters 35(25): 4383-4386.
Kobayashi, et al., "Niphatesines E-H, New Pyridine Alkaloids from the Okinawan Marine Sponge *niphates* Sp." Journal of the Chemical Society-Perkin Transactions 1 1992, (11), 1291-1294.
Krauss, et al., (2004). "A new approach towards ikimine A analogues." Natural Product Research 18(5): 397-401.
Kura, et al., (2011). "Pyrinodemins E and F, new 3-alkylpyridine alkaloids from sponge *amphimedon* sp." Bioorganic & Medicinal Chemistry Letters 21(1): 267-270.
Laville, et al., (2009). "Njaoaminiums A, B, and C: Cyclic 3-Alkylpyridinium Salts from the Marine Sponge *reniera* sp." Molecules 14(11): 4716-4724.
Laville, et al., (2008). "Pachychalines A-C: Novel 3-alkylpyridinium salts from the marine sponge *pachychalina* sp." European Journal of Organic Chemistry(1): 121-125.
Leyssen et al., "Perspectives for the treatment of infections with Flaviviridae". Clinical microbiology reviews 2000, 13 (1), 67-82, table of contents.
Matsunaga, et al., (1993). "Bioactive Marine Metabolites .53. Cribrochalinamine Oxide-a and Oxide-B, Antifungal Beta-Substituted Pyridines with an Azomethine N-Oxide from a Marine Sponge *cribrochalina* Sp." Tetrahedron Letters 34(37): 5953-5954.
Oku, et al., (2004). "Three new cyclostellettamines, which inhibit histone deacetylase, from a marine sponge of the genus *Xestospongia*." Bioorganic & Medicinal Chemistry Letters 14(10): 2617-2620.
O'Rourke, Aubrie Elise, "Bioprospecting of Red Sea Sponges for Novel Anti-Viral Pharmacophores", PhD thesis, King Abdullah University of Science and Technology (2015).
Seleghim et al., "Antibiotic, cytotoxic and enzyme inhibitory activity of crude extracts from Brazilian marine invertebrates", Revista

(56) References Cited

OTHER PUBLICATIONS

Brasileira De Farmacognosia, (Jul. 1, 2007) Retrieved from the Internet: URL:http://www.scielo.br/pdf/rbfar/v17n3/01.pdf.

Schmitz, et al., (1978). "Marine Natural-Products—Halitoxin, Toxic Complex of Several Marine Sponges of Genus *Haliclona*." Journal of Organic Chemistry 43(20): 3916-3922.

Scott, et al., (2000). "Analysis of the structure and electrophysiological actions of halitoxins: 1,3 alkyl-pyridinium salts from Callyspongia ridleyi." Journal of Membrane Biology 176(2): 119-131.

Sepcic et al., "Biological activities of aqueous extracts from marine sponges and cytotoxic effects of 3-alkylpyridinium polymers from Reniera sarai". Comp Biochem Physiol C Pharmacol Toxicol Endocrinol 1997, 117 (1), 47-53.

Teruya, et al., (2006). "Cyclohaliclonamines A-E: Dimeric, trimeric, tetrameric, pentameric, and hexameric 3-alkyl pyridinium alkaloids from a marine sponge *haliclona* sp." Journal of Natural Products 69(1): 135-137.

Timm et al., "Synthesis of 3-Alkyl Pyridinium Alkaloids from the Arctic Sponge *Haliclona viscosa*",Mar. Drugs 2010, 8, 483-497.

Timm et al., "The first cyclic monomeric 3-alkylpyridinium alkaloid from natural sources: identification, synthesis and biological activity", Organic & Biomolecular Chemistry, vol. 6. (2008) pp. 4036-4040.

Tiraboschi et al., "Evaluating voting competence in persons with Alzheimer disease". International journal of Alzheimer's disease 2011, 2011, 983895.

Tsuda, et al., (1999). "Pyrinodemin A, a cytotoxic pyridine alkaloid with an isoxazolidine moiety from sponge *amphimedon* sp." Tetrahedron Letters 40(26): 4819-4820.

Tsukamoto, S., M. et al., (2000). "Hachijodines A-G: Seven new cytotoxic 3-alkylpyridine alkaloids from two marine sponges of the genera *Xestospongia* and *Amphimedon*." Journal of Natural Products 63(5): 682-684.

Tucker et al., "The influence of alkyl pyridinium sponge toxins on membrane properties, cytotoxicity, transfection and protein expression in mammalian cells". Biochimica Et Biophysica Acta-Biomembranes 2003, 1614 (2), 171-181.

Volk, et al., (2004). "Viscosaline: new 3-alkyl pyridinium alkaloid from the Arctic sponge *Haliclona viscosa*." Organic & Biomolecular Chemistry 2(13): 1827-1830.

Yu et al., "Macrocyclic drugs and synthetic methodologies toward macrocycles". Molecules 2013, 18 (6), 6230-68.

\* cited by examiner

[Bar chart: % Activity wNV NS3 protease (test/control) vs SPE fraction of A. chloros]
- SPE F2: ~8%
- SPE F3: ~98%
- SPE F4: ~94%

B

[Bar chart: % Activity WNV NS3 protease vs Dilution of SPE fraction 2]
- 37.5ug/ml: ~27%
- 18.75ug/ml: ~29%
- 9.38ug/ml: ~32%
- 4.69ug/ml: ~40%

FIGURE 5

3-ALKYL PYRIDINIUM COMPOUND FROM RED SEA SPONGE WITH POTENT ANTIVIRAL ACTIVITY

CROSS REFERENCE TO RELATED APPLICATION

This is a national stage application of PCT/IB2015/002187, filed internationally on Oct. 29, 2015, which claims priority to U.S. Provisional Application Ser. No. 62/072,292, filed on Oct. 29, 2014, both of which are incorporated by reference herein in their entireties.

BACKGROUND

Viral infections are a major cause of disease and death among the world's population. Important viral pathogens include, for example, human immunodeficiency virus-1 (HIV-1), influenza virus, several forms of hepatitis viruses (HAV, HBV, HCV), herpes viruses (HSV, VZV, EBV, CMV) and a whole panel of arthropode-borne viruses, such as yellow fever virus, dengue virus, west nile virus, among others. Several viruses cause chronic diseases that require life-long treatment. HIV-1, the causative agent of AIDS, is one important example of a chronic viral pathogen and is still a major global health problem, with more than 33 million infected individuals worldwide. Other viruses, such as influenza, show pandemic spread on a frequent basis causing tens of thousands deaths around the world almost every year. In addition, many viruses are known to cause cancer, with T-cell leukaemia (HTLV), cervical cancer (HPV) and liver cancer (HBV, HCV) being prominent examples. It is estimated that 10-20% of all cancers are actually of viral origin.

While vaccines or antiviral drugs are available for a number of viruses, no specific antiviral therapy is available for the great majority of viral pathogens. However, antiviral research has grown dramatically in the past two decades, and the antiviral market has an average growth rate of 16.7% and an expected total volume of $29.4 billion in 2015 ($23.4 billion in 2008). The global antiviral market represents about half of the overall anti-infective market. Antivirals are increasingly important in emerging markets and in markets in less-developed countries where prices may be lower but volumes can be greater. These regions of the world often experience the most severe outbreaks of viral pathogens.

Currently (United States) approved antivirals target infections by the human immunodeficiency virus (HIV), hepatitis B virus (HBV), hepatitis C virus (HCV), influenza virus, and several herpes viruses. HCV, a flavivirus, has been the focus of intense drug discovery efforts. Recently (May 2011) two protease inhibitors (INCIVEK™, Vertex; Victrelis®, Merck) were fully approved by the FDA for the treatment of chronic hepatitis C infection in combination with pegylated interferon and ribavirin. More than 34 further anti-HCV drugs are in various clinical phases.

While HCV has gained much attention in the field of vaccines and antivirals, other members of the same virus family, flaviviruses, lack far behind. While at least a vaccine is available for yellow fever virus (YFV), two other major pathogens of the flavivirus group, dengue virus (DENV) and West Nile (WNV) virus, currently lack any possibility of a specific antiviral intervention. Dengue virus is the most widespread arthropod-borne virus and is expanding its geographical habitat, due to global climate change. Worldwide, there are approximately 2.5 billion people at risk of infection, with an estimated 40-100 million incidences of dengue infection and about 500,000 hospitalizations due to dengue haemorrhagic fever annually. With a third of the world's population at risk of infection, the World Health Organization (WHO) has made it a priority to develop a treatment/vaccine for the past three decades to no avail. The city of Jeddah, Saudi Arabia, for example, has a particularly high risk for the occurrences of dengue due to the high influx of pilgrims from Indonesia, Malaysia, and Thailand (all high-burden dengue countries). WNV causes a fever with possible neurological involvement. The virus has spread globally with several epidemics in the US. The worst outbreak in the US occurred in 2012 with 286 deaths, mainly in the state of Texas. Despite the availability of an effective vaccine, the WHO estimates that there are still 200,000 infections and approximately 30,000 deaths per year related to yellow fever. An infection with YFV can cause a serious hemorrhagic fever. As for DENV and WNV, there is no specific antiviral treatment available for the yellow fever disease.

Hence, a need exists for better antiviral agents, particularly with respect to flaviviruses including West Nile Virus, for example. HIV is another important target.

SUMMARY

Embodiments described herein include compounds and compositions, methods of providing, isolating, and purifying the compounds and compositions, and methods of using the compounds and compositions including treatment of living persons and animals.

For example, one aspect provides for a method for treating a viral infection in a patient, comprising administering to the patient a therapeutically effective amount of a compound, or a pharmaceutically acceptable salt thereof, comprising at least one moiety represented by Formula (1):

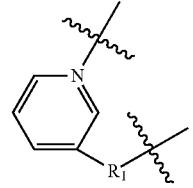

Formula (1)

wherein $R_1$ is a saturated or unsaturated bivalent hydrocarbon group.

In another embodiment, the moiety is represented by Formula (2):

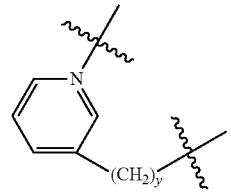

Formula (2)

wherein y is 5-15.

In another embodiment, the compound is represented by Formula (3):

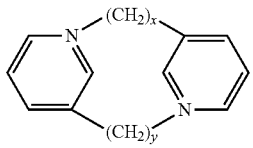

Formula (3)

wherein x and y, independently of each other, are each 5-15.

In another embodiment, the compound is represented by Formula (4):

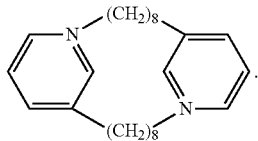

Formula (4)

In one embodiment, the compound comprises at least two moieties represented by Formula (1). In one embodiment, the compound comprises at least two moieties represented by Formula (2).

In one embodiment, the compound is not a salt. In one embodiment, the compound is a pharmaceutically acceptable salt.

In one embodiment, the patient is infected with a retrovirus. In another embodiment, the patient is infected with a lentivirus. In another embodiment, the patient is infected with an HIV virus. In another embodiment, the patient is infected with an HIV-1 virus. In another embodiment, the patient is infected with a flavivirus virus. In another embodiment, the patient is infected with a dengue virus. In another embodiment, the patient is infected with a West Nile virus. In another embodiment, the patient is infected with a hepatitis C virus. In another embodiment, the patient is infected with a yellow fever virus.

In another embodiment, the therapeutically effective amount is provided in the form of a solid having an amount of active ingredient of at least 1 wt. %. In another embodiment, the therapeutically effective amount is provided in the form of a solid having an amount of active ingredient of at least 5 wt. %.

Another aspect provides for a composition comprising: a compound, or a pharmaceutically acceptable salt thereof, comprising a moiety represented by Formula (1):

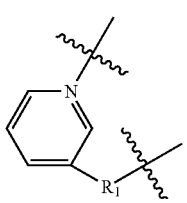

Formula (1)

wherein $R_1$ is a saturated or unsaturated bivalent hydrocarbon group.

In another embodiment, the moiety is represented by Formula (2):

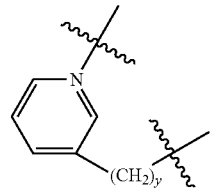

Formula (2)

wherein y is 5-15.

In another embodiment, the compound is represented by Formula (3):

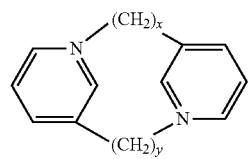

Formula (3)

wherein x and y, independently of each other, are each 5-15.

In another embodiment, the compound is represented by Formula (4):

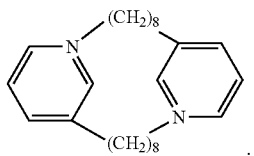

Formula (4)

In one embodiment, the compound is not a salt. In another embodiment, the compound is a pharmaceutically acceptable salt.

Another embodiment provides that the composition consisting essentially of, or consists of, an isolated and purified form of the compound, or a pharmaceutically acceptable salt thereof. This includes the compound, or a pharmaceutically acceptable salt thereof, comprising a moiety represented by Formula (1) or Formula (2), and well as the compounds, or a pharmaceutically acceptable salt thereof, represented by Formulae (3) or (4).

Another aspect is a method of isolation and purification comprising: isolating and purifying the composition described herein from a natural source.

In one embodiment, the natural source is from the Red Sea. In another embodiment, the natural source is from a Red Sea sponge. In another embodiment, the natural source is from a sponge *Echinochalina*. In another embodiment, the natural source is from a Red Sea sponge *Amphimedon chloros*.

Another aspect is a method for treating a viral infection in a patient, comprising administering to the patient a therapeutically effective amount of a compound, or a pharmaceutically acceptable salt thereof, which inhibits NS3 protease.

Another aspect is a method for treating a viral infection in a patient, comprising administering to the patient a therapeutically effective amount of a compound, or a pharmaceutically acceptable salt thereof, comprising at least one alkyl pyridinium compound. The alkyl pyridinium compound, or pharmaceutically acceptable salt thereof, can be a 3-alkyl pyridinium compound. The alkyl pyridinium compound, or pharmaceutically acceptable salt thereof, can be a polymer alkyl pyridinium compound. The number average molecular weight can be, for example, 30,000 daltons (g/mol) to 50,000 daltons (g/mol).

At least one advantage for at least some embodiments includes productive treatment of persons, animals, or any living object who or which might be or have been infected with a virus.

BRIEF DESCRIPTION OF THE DRAWINGS

FIG. 2 shows SPE (solid phase extracts) fraction activity.

FIG. 5: Activity of *A. chloros* on the WNV NS3 protease. (A) Biological replicates (s10, s16, s36, and C16) of *A. chloros* SPE fraction 2, 3 and 4 (SPE F2, F3, F4) screened at approximately 37.5 μg/ml for activity against WNV NS3 protease SPE F2 shows an inhibition of the protease. (B) Serial dilutions of two biological replicates of *A. chloros* SPE fraction 2 were screened against NS3 protease and maintain up to 60% inhibition of the protease at a concentration of 4.69 μg/ml.

FIG. 6: Vitality of cells treated with HPLC fractions from the SPE fraction 2 (SPE F2) of *A. chloros*. Cell counts of the HeLa cells cultures treated with the test compound isolated from biological replicates (s10, s16, s36, and C16) of *A. chloros* show that the first dilution (230 μg/ml) results in 60% cell death. The following serial dilutions (115 μg/ml and 57.5 μg/ml) approach 100% vitality. This can be compared to the 37.5 μg/ml used in the WNV screen and shows us this concentration is expected to have cell vitality around 80%.

FIGS. 7A-D: Analytical chemistry of active SPE fraction 2 from *A. chloros* (A) LC-MS reveals the main substituent of the bioactive *A. chloros* SPE fraction 2 to be the parent m/z [M+H]+ 379 and its daughter at m/z [M+H]+ 190.15. (B, C) 1H NMR from Davies-Coleman publication and from this study. The 1H NMR reported in the Supplemental material of Davies-Coleman (B) and our 1H spectra (C) present the same signals. Their findings and ours, reported in brackets, are as follows: delta 8.95 [9.00], 8.84 [8.91], 8.45 [8.45], 8.01 [8.07] that are attributed to the 3-substituted pyridinium salt; delta at 4.60 [4.66] attributed to the methylene group on the quaternary nitrogen, which is coupled to a methylene signal at 2.20 [2.21], further coupled to a methylene envelope at delta 1.41 [1.41]; and a signal at delta 2.87 [2.87] assigned to the methylene group bound to the C-3 position of the pyridinium ring, coupled to a methylene signal at delta 1.73 [1.73]. Also observed is the presence of a peak at delta 1.31 in both spectra, but with great intensity in the present sample, which is assumed associated with the methylene envelope at delta 1.41. A solvent phase shift for the deuterated methanol—d4 at 3.31 ppm and 4.87 ppm was observed as expected. (D) 2D DOSY diffusion variable gradient was calculated for the most intense peak at delta 1.31. The gradient is pictured above and provided the following coefficient of diffusion: 1.34 E-10m2/s, which was used to estimate the molecular weight of the compound using the Evans et al. 2013.

DETAILED DESCRIPTION

Introduction

U.S. priority provisional application 62/072,292 filed Oct. 29, 2014 is hereby incorporated by reference.

The following PhD thesis is incorporated herein by reference: "Bioprospecting of Red Sea Sponges for Novel Anti-Viral Pharmacopoeias," Aubrie Elise O'Rourke, 2015, King Abdullah University of Science and Technology, Thuwal, Kingdom of Saudi Arabia; including Chapters 1 and 2 in particular.

References cited herein are incorporated by reference.

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs. Unless clearly contraindicated by the context each compound name includes the free acid or free base form of the compound as well hydrates of the compound and all pharmaceutically acceptable salts of the compound.

The transition term "comprising" is an open-ended term and includes within its scope the transition terms "consisting essentially of," or equivalently "consists essentially of," and "consists of."

A composition which has an isolated or purified compound or component can include, for example, at least 80 wt. %, or at least 90 wt. %, or at least 95 wt. %, or at least 98 wt. %, or at least 99 wt. % of the compound or component.

A term such as "Formula X" such as, for example, Formula 1, Formula 2, Formula 3, or Formula 4, encompasses all groups compounds that satisfy Formula X, including any enantiomers, racemates and stereoisomers, as well as all pharmaceutically acceptable salts of such compounds. The phrase "a compound of Formula X" includes all subgeneric groups and compounds of Formula X as well as all forms of such compounds, including salts and hydrates, unless clearly contraindicated by the context in which this phrase is used.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including a compound of the invention), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline forms, and any polymorphs of the compound are included. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

Figure 1:
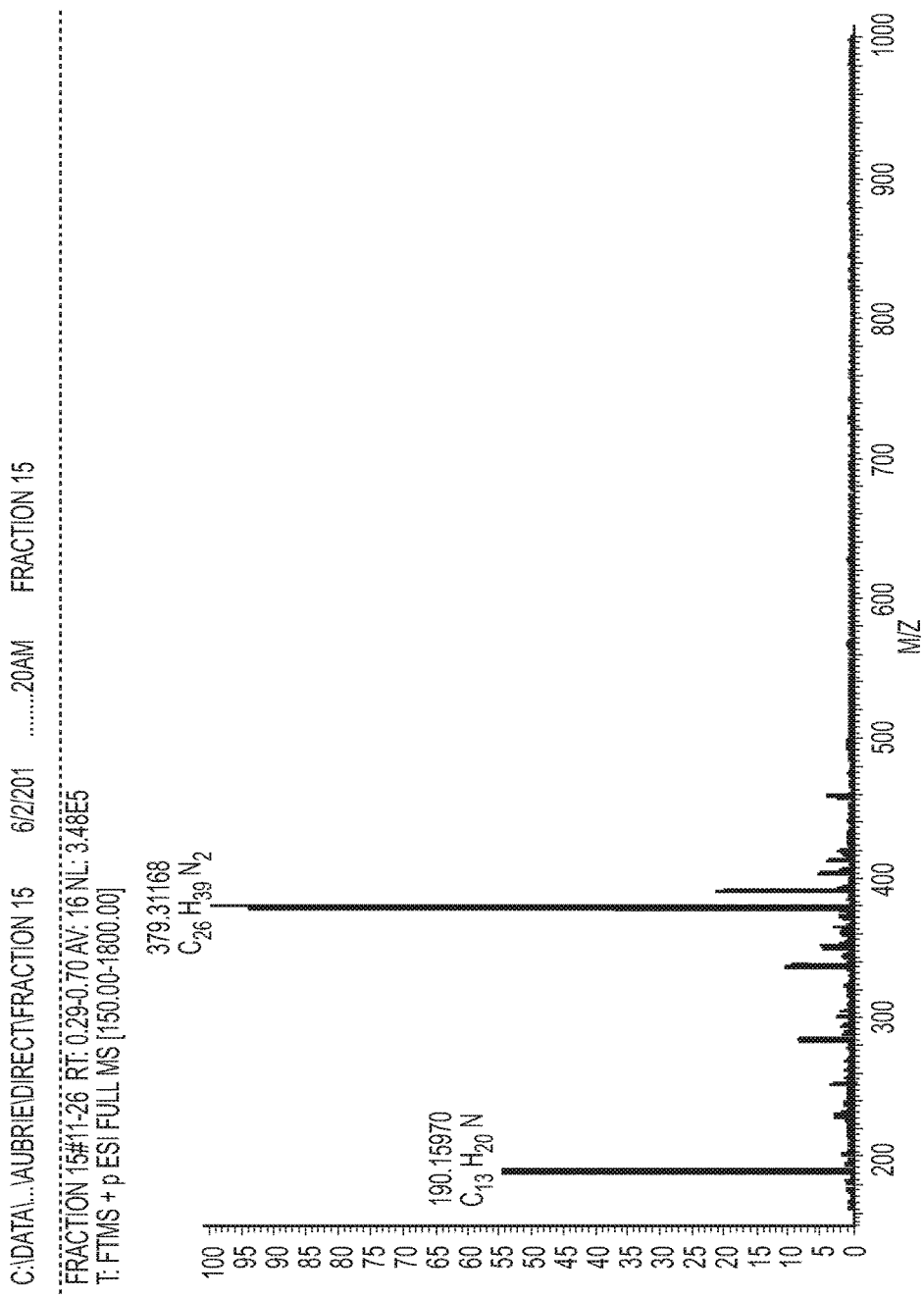
FIG. 1 shows mass spectral analysis: $MS^2$ of compound 1 after fragmentation.

A dash ("-") that is not between two letters or symbols is used to indicate a point of attachment for a substituent. For example, —$(CH_2)C_3$-$C_8$ cycloalkyl is attached through carbon of the methylene ($CH_2$) group.

"Alkanoyl" indicates an alkyl group as defined herein, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

"Alkyl" is a branched or straight chain saturated aliphatic hydrocarbon group having the specified number of carbon atoms, generally from 1 to about 12 carbon atoms. The term $C_1$-$C_6$ alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_6$ alkyl, $C_1$-$C_4$ alkyl, and $C_1$-$C_2$ alkyl. When $C_0$-$C_n$ alkyl is used herein in conjunction with another group; for example, (cycloalkyl)$C_0$-$C_4$ alkyl, the indicated group, in this case cycloalkyl, is either directly bound by a single covalent bond ($C_0$), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl.

"Alkylene" is a bivalent branched or straight chain saturated aliphatic hydrocarbon group having the specified number of carbon atoms, generally from 1 to about 12 carbon atoms. The term $C_1$-$C_6$ alkylene as used herein indicates an alkylene group having from 1, 2, 3, 4, 5, or 6 carbon atoms. Other embodiments include alkylene groups having from 1 to 8 carbon atoms, 1 to 4 carbon atoms or 1 or 2 carbon atoms, e.g. $C_1$-$C_6$ alkylene, $C_1$-$C_4$ alkylene, and $C_1$-$C_2$ alkylene. When $C_0$-$C_n$ alkylene is used herein in conjunction with another group; for example, (cycloalkyl)$C_0$-$C_4$ alkylene, the indicated group, in this case cycloalkyl, is either directly bound by a single covalent bond ($C_0$), or attached by an alkyl chain having the specified number of carbon atoms, in this case 1, 2, 3, or 4 carbon atoms. Examples of alkylene include, but are not limited to, methylene, ethylene, propylene, butylene, pentylene, hexylene, heptylene, and octylene.

"Alkoxy" indicates an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. When "$C_0$-$C_n$ alkoxy" is used in with another group, for example, (heteroaryl)$C_0$-$C_4$ alkoxy, the indicated group, in this case heteroaryl, is either attached via a covalently bound oxygen bridge ($C_0$ alkoxy), or attached by an alkoxy group having the specified number of carbon atoms, in this case from 1 to about 4 carbon atoms, that is covalently bound to the group it substitutes via the alkoxy oxygen atom.

"Cycloalkyl" is a saturated hydrocarbon ring group, having the specified number of carbon atoms. Monocyclic cycloalkyl groups typically have from 3 to about 8 carbon ring atoms or from 3 to 7 (3, 4, 5, 6, or 7) carbon ring atoms. Cycloalkyl substituents may be pendant from a substituted nitrogen or carbon atom, or a substituted carbon atom that may have two substituents may have a cycloalkyl group, which is attached as a spiro group. Examples of cycloalkyl groups include cyclopropyl, cyclobutyl, cyclopentyl, or cyclohexyl as well as bridged or caged saturated ring groups such as norbornane or adamantane.

The terms "(cycloalkyl)$C_0$-$C_n$ alkyl" indicates a substituent in which the cycloalkyl and alkyl are as defined herein, and the point of attachment of the (cycloalkyl)alkyl group to the molecule it substitutes is either a single covalent bond, ($C_0$ alkyl) or on the alkyl group. (Cycloalkyl)alkyl encompasses, but is not limited to, cyclopropylmethyl, cyclohexylmethyl, and cyclohexylmethyl.

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Halo" or "halogen" indicates any of fluoro, chloro, bromo, and iodo.

The term "substituted", as used herein, means that any one or more hydrogens on the designated atom or group is replaced with a selection from the indicated group, provided that the designated atom's normal valence is not exceeded. For example, when the substituent is oxo (i.e., =O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

"Optionally substituted" is a term known in the art. Substituents which can be present optionally include, for example, alkanoyl, alkyl, alkoxy, cycloalkyl, haloalkyl, haloalkoxy, and halo or halogen, as well as any other functional group known in the art and/or described herein.

Unless otherwise specified, substituents are named into the core structure. For example, it is to be understood that when (cycloalkyl)alkyl is listed as a possible substituent the point of attachment of this substituent to the core structure is in the alkyl portion.

Suitable groups that may be present on a "substituted" position include, but are not limited to, e.g., halogen; cyano; hydroxyl; nitro; azido; alkanoyl (such as a $C_2$-$C_6$ alkanoyl group such as acyl or the like); carboxamido; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, such as a compound or salt as described herein, and at least one other substance, such as a carrier. Pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in Remington's Pharmaceutical Sciences, 17th ed., Mack Publishing Company, Easton, Pa., p. 1418 (1985).

The term "carrier" applied to pharmaceutical compositions of the invention refers to a diluent, excipient, or vehicle with which an active compound is provided.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Providing a compound of Formula X with at least one additional active agent" means the compound of Formula X and the additional active agent(s) are provided simultaneously in a single dosage form, provided concomitantly in separate dosage forms, or provided in separate dosage forms for administration separated by some amount of time that is within the time in which both the compound of Formula X and the at least one additional active agent are within the blood stream of a patient. The compound of Formula X and the additional active agent need not be prescribed for a patient by the same medical care worker. The additional active agent or agents need not require a prescription. Administration of the compound of Formula X or the at least one additional active agent can occur via any appropriate route, for example, oral tablets, oral capsules, oral liquids, inhalation, injection, suppositories or topical contact.

"Treatment," as used herein includes providing a compound of Formula X, either as the only active agent or together with at least one additional active agent sufficient to: (a) prevent a disease or a symptom of a disease from occurring in a patient who may be predisposed to the disease but has not yet been diagnosed as having it (e.g. including diseases that may be associated with or caused by a primary disease (as in, for example, liver fibrosis that can result in the context of chronic HCV infection); (b) inhibiting the disease, i.e. arresting its development; and (c) relieving the disease, i.e., causing regression of the disease. "Treating" and "treatment" also means providing a therapeutically effective amount of a compound of Formula X, as the only active agent or together with at least one additional active agent to a patient having or susceptible to a viral infection.

A "therapeutically effective amount" of a pharmaceutical combination of this invention means an amount effective, when administered to a patient, to provide a therapeutic benefit such as an amelioration of symptoms, e.g., an amount effective to decrease the symptoms of a viral infection such as a hepatitis C infection. For example a patient infected with a virus such as, for example, a hepatitis C virus may present elevated levels of certain liver enzymes, including AST and ALT. In this example, normal levels of AST are from 5 to 40 units per liter of serum (the liquid part of the blood) and normal levels of ALT are from 7 to 56 units per liter of serum. In this example, a therapeutically effect amount is thus an amount sufficient to provide a significant reduction in elevated AST and ALT levels or an amount sufficient to provide a return of AST and ALT levels to the normal range. A therapeutically effective amount is also an amount sufficient to prevent a significant increase or significantly reduce the detectable level of virus or viral antibodies in the patient's blood, serum, or tissues.

A significant increase or reduction in the detectable level of virus or viral antibodies is any detectable change that is statistically significant in a standard parametric test of statistical significance such as Student's T-test, where $p<0.05$.

Method of Treatment

Methods of treatment can include methods of preventing viral infection and methods of treating viral infections. Provided herein is a method for treating a viral infection in a patient, comprising administering to the patient a therapeutically effective amount of a compound as described herein. Patient can be broadly interpreted to include humans and animals. The patient may or may not be infected with the target virus at the time of administrating to the patient.

Sources of Materials to be Screened and Screening

Sources of products include, for example, algae, invertebrates, bacterial isolates, sponges, and items taken from the deep sea including deep sea sponges.

Sponges of type *Amphimedon chloros* are known including coming from the Red Sea.

Sponges of the *Echinochalina* type are also known. See, for example, Jimenez, et al., (2000). "Upenamide: An unprecedented macrocyclic alkaloid from the Indonesian sponge *Echinochalina* sp." *Journal of Organic Chemistry* 65(25): 8465-8469.

Bioactive screening programs can be carried out using Red Sea invertebrates.

Screening methods and high throughput screening (HTS) are known in the art. See, for example, Bugni, et al., (2008). "Fractionated marine invertebrate extract libraries for drug discovery." *Molecules* 13(6): 1372-1383. Methods and tools known in the art such as, for example, fluorescent imaging and quantitative analysis, self organizing maps (SOMs) and cluster analysis can be used. An example of an instrument and screening system is the Thermo Scientific Cellomics Arrayscan VTI. Reference libraries can be used such as, for example, Sigma Aldrich LOPAC1280.

Purification Methods

Separation, purification, and isolation methods known in the art can be carried out.

Solid phase extracts (SPE) can be isolated.

One exemplary method is fractioning a crude methanol extract using HP20SS bead and then desalting with water and eluting with 1:1 water/isopropanol, from a Red Sea sponge.

Alkylpyridinium Compounds, Dimers, Oligomers, Polymers

Alkylpyridinium compounds are known in the art including different forms such as linear and cyclic forms. Also known are isolation, characterization, and bioactivity testing methods. See, for example, Davies-Coleman, et al., (1993). "A New Egf-Active Polymeric Pyridinium Alkaloid from the Sponge *Callyspongia-Fibrosa.*" *Journal of Organic Chemistry* 58(22): 5925-5930; Teruya, et al., (2006). "Cyclohaliclonamines A-E: Dimeric, trimeric, tetrameric, pentameric, and hexameric 3-alkyl pyridinium alkaloids from a marine sponge *Haliclona* sp." *Journal of Natural Products* 69(1): 135-137; Oku, et al., (2004). "Three new cyclostellettamines, which inhibit histone deacetylase, from a marine sponge of the genus *Xestospongia.*" *Bioorganic & Medicinal Chemistry Letters* 14(10): 2617-2620; and Bugni, et al., (2008). "Fractionated marine invertebrate extract libraries for drug discovery." *Molecules* 13(6): 1372-1383.

See also: Volk, et al., (2004). "Viscosaline: new 3-alkyl pyridinium alkaloid from the Arctic sponge *Haliclona viscosa.*" *Organic & Biomolecular Chemistry* 2(13): 1827-1830; Cutignano, et al., (2004). "Polyketide origin of 3-alkylpyridines in the marine mollusc *Haminoea orbignyana.*" *Tetrahedron Letters* 45(12): 2627-2629; Damodaran, V., et al., (2013). "Cyclic 3-Alkyl Pyridinium Alkaloid Monomers from a New Zealand *Haliclona* sp. Marine Sponge." *Journal of Natural Products* 76(10): 1997-2001; Hirano, et al., (2000) "Pyrinodemins B-D, potent cytotoxic bis-pyridine alkaloids from marine sponge *Amphimedon* sp." *Chemical & Pharmaceutical Bulletin* 48(7): 974-977; Kariya, et al., (2006). "Pyrinadines B-G, new bis-pyridine alkaloids with an azoxy moiety from sponge *Cribrochalina* sp." *Bioorganic & Medicinal Chemistry* 14(24): 8415-8419; Kariya, et al., (2006). "Pyrinadine A, a novel pyridine alkaloid with an azoxy moiety from sponge *Cribrochalina* sp." *Tetrahedron Letters* 47(6): 997-998; Kobayashi, et al., (1990). "Niphatesines a-D, New Antineoplastic Pyridine Alkaloids from the Okinawan Marine Sponge *Niphates* Sp." *Journal of the Chemical Society-Perkin Transactions* 1(12): 3301-3303; Krauss, et al., (2004). "A new approach towards ikimine A analogues." *Natural Product Research* 18(5): 397-401; Kura, et al., (2011). "Pyrinodemins E and F, new 3-alkylpyridine alkaloids from sponge *Amphimedon* sp." *Bioorganic & Medicinal Chemistry Letters* 21(1): 267-270; Laville, et al., (2009). "Njaoaminiums A, B, and C: Cyclic 3-Alkylpyridinium Salts from the Marine Sponge *Reniera* sp." *Molecules* 14(11): 4716-4724; Laville, et al., (2008). "Pachychalines A-C: Novel 3-alkylpyridinium salts from the marine sponge *Pachychalina* sp." *European Journal of Organic Chemistry*(1): 121-125; Schmitz, et al., (1978). "Marine Natural-Products—Halitoxin, Toxic Complex of Several Marine Sponges of Genus *Haliclona.*" *Journal of Organic Chemistry* 43(20): 3916-3922; Tsuda, et al., (1999). "Pyrinodemin A, a cytotoxic pyridine alkaloid with an isoxazolidine moiety from sponge *Amphimedon* sp." *Tetrahedron Letters* 40(26): 4819-4820; Tsukamoto, S., M. et al., (2000). "Hachijodines A-G: Seven new cytotoxic 3-alkylpyridine alkaloids from two marine sponges of the genera *Xestospongia* and *Amphimedon.*" *Journal of Natural Products* 63(5): 682-684; Matsunaga, et al., (1993). "Bioactive Marine Metabolites. 53. Cribrochalinamine Oxide-a and Oxide-B, Antifungal Beta-Substituted Pyridines with an Azomethine N-Oxide from a Marine Sponge *Cribrochalina*

Sp." *Tetrahedron Letters* 34(37): 5953-5954; Kobayashi, et al., (1989). "Theonelladins-a-D, Novel Antineoplastic Pyridine Alkaloids from the Okinawan Marine Sponge *Theonella-Swinhoei.*" *Tetrahedron Letters* 30(36): 4833-4836; Albrizio, et al., (1995). "Amphitoxin, a New High-Molecular-Weight Antifeedant Pyridinium Salt from the Caribbean Sponge *Amphimedon Compressa.*" *Journal of Natural Products* 58(5): 647-652; Arai, et al., (2009). "Haliclonacyclamines, tetracyclic alkylpiperidine alkaloids, as anti-dormant mycobacterial substances from a marine sponge of *Haliclona* sp." *Chem Pharm Bull (Tokyo)* 57(10): 1136-1138; Scott, et al., (2000). "Analysis of the structure and electrophysiological actions of halitoxins: 1,3 alkyl-pyridinium salts from *Callyspongia ridleyi.*" *Journal of Membrane Biology* 176(2): 119-131. See, also, Gil et al., *Tetrahedron Letters,* 36, 12, 2059-2062, 1995; Timm et al., *Mar. Drugs* 2010, 8, 483-497.

Related compounds are also described in Defant, A., et al., (2011). "New Structural Insights into Saraines A, B, and C, Macrocyclic Alkaloids from the Mediterranean Sponge *Reniera* (*Haliclona*) *sarai.*" *European Journal of Organic Chemistry* (20-21): 3761-3767; Kobayashi, et al., (1994). "Keramaphidin-B, a Novel Pentacyclic Alkaloid from a Marine Sponge *Amphimedon* Sp—a Plausible Biogenetic Precursor of Manzamine Alkaloids." *Tetrahedron Letters* 35(25): 4383-4386; US Patent Publication Nos. 2002/0187999 and 2005/0159400; and WO 2005/084157.

Without being bound by any particular theory, it is believed that the active ingredients act as inhibitor for an NS3 protease.

One embodiment provides a compound, or a pharmaceutically acceptable salt thereof, comprising at least one moiety represented by Formula (1):

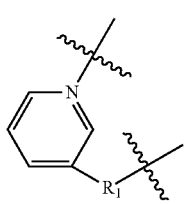

Formula (1)

wherein $R_1$ is a saturated or unsaturated bivalent hydrocarbon group. $R_1$ can be, for example, a $C_5$-$C_{15}$ group, or a $C_5$-$C_{10}$ group, or a $C_7$-C10 group, or a $C_7$-$C_9$ group, or can be $C_8$. Preferably, $R_1$ is saturated. The hydrocarbon group can be, for example, an alkylene group. The $R_1$ group is optionally substituted, but preferably is unsubstituted. The $R_1$ group preferably only has carbon and hydrogen atoms. The $R_1$ group of Formula (1) preferably covalently binds to a pyridine ring, as shown, for example, in Formulae (3) and (4). The N atom of the pyridine ring in Formula (1) preferably covalently binds to another $R_1$ bivalent group, as shown, for example, in Formulae (3) and (4). Oligomeric and/or polymeric structures can be formed, and the number average molecular weight can be measured as described herein. The moiety shown in Formula (1) can be repeated, for example up to 500 times, or up to 300 times, or up to 150 times to provide the described molecular weight.

In some embodiments, the pyridine ring of Formula (1) can be further substituted.

In another embodiment, the moiety is represented by Formula (2):

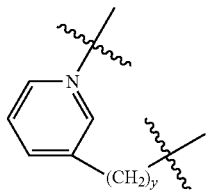

Formula (2)

wherein y is 5-15. Y can be, for example, 7-10, or 8. In some embodiments, the pyridine ring of Formula (2) can be further substituted. The —$(CH_2)_y$— group of Formula (2) preferably covalently binds to a pyridine ring, as shown, for example, in Formulae (3) and (4). The N atom of the pyridine ring in Formula (2) preferably covalently binds to another $R_1$ bivalent group, as shown, for example, in Formulae (3) and (4).

In another embodiment, the compound is represented by Formula (3):

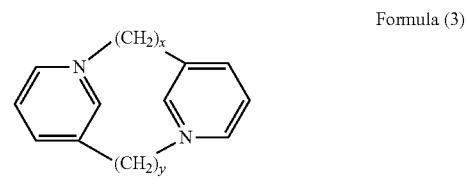

Formula (3)

wherein x and y, independently of each other, are each 5-15, or can be, for example, 7-10 or 8. In some embodiments, one or both the pyridine rings of Formula (3) can be further substituted.

In another embodiment, the compound is represented by Formula (4):

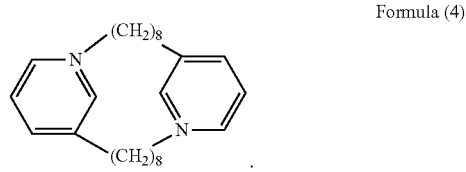

Formula (4)

In some embodiments, one or both of the pyridine rings of Formula (4) can be further substituted.

In one embodiment, the compound comprises at least two moieties represented by Formula (1). In one embodiment, the compound comprises at least two moieties represented by Formula (2).

In one embodiment, the compound is not a salt. In another embodiment, the compound is a pharmaceutically acceptable salt.

The number average molecular weight of the compound can vary. For example, the number average molecular weight can be, for example, 250 daltons to 100,000 daltons, or 1,000 daltons to 100,000 daltons, or 2,000 daltons to 75,000 daltons, or 5,000 daltons to 50,000 daltons, or 30,000 daltons to 50,000 daltons.

Compositions

Compounds as described herein can be administered as the neat chemical, but are preferably administered as a pharmaceutical composition. Accordingly, the invention provides pharmaceutical compositions comprising a compound or pharmaceutically acceptable salt as described herein, together with at least one pharmaceutically acceptable carrier. The pharmaceutical composition may contain a compound or salt as described herein as the only active agent, or may contain one or more additional active agents.

Compounds and compositions as described herein may be administered by various methods including, for example, orally, topically, parenterally, by inhalation or spray, sublingually, transdermally, via buccal administration, rectally, as an ophthalmic solution, or by other means, in dosage unit formulations containing conventional pharmaceutically acceptable carriers. More particularly, the compositions can be in a wide variety of forms including, for example, the form of tablets, pills, hard capsules, soft capsules, liquids, suspensions, emulsified form, syrup, and granules. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the active ingredient.

For example, the pharmaceutical compositions can be formulated for oral administration. These compositions can be in the form of a solid and can contain, for example, between 0.1 and 99 weight % (wt. %) of active ingredient compound and usually at least about 0.1 wt. % of active ingredient compound, usually at least about 1 wt. % of active ingredient compound, or at least about 5 wt. % of active ingredient compound. Some embodiments contain from about 25 wt. % to about 50 wt. % or from about 5 wt. % to about 75 wt. % of the active ingredient compound.

Mixtures of active ingredients can be used, whether the active ingredients are the same type of molecule (e.g., types as shown in Formulae 1, 2, or 3), or different types of molecules.

NS3 Proteases as Drug Targets

Flavivirus and NS3 protease are known in the art. See, for example, U.S. Pat. Nos. 8,778,876; 8,097,728; 8,030,318; 7,977,342; and 7,491,794.

While the market for HCV therapeutics is potentially shrinking due to better control of transmission and more effective treatments, the problem with other flaviviruses is increasing and therefore expected to soon join the list of diseases with economically rewarding drug markets. To date there are no anti-DENV, anti-WNV or anti-YFV drugs in advanced clinical trials.

The flaviviral NS3 protease catalyzes the processing of the viral polyprotein. Correct processing of this precursor protein is essential for the viral life cycle and makes this enzyme an ideal target for drug development. The flaviviral protease is a serine protease and is dependent on association with a hydrophilic region of the NS2B protein, which acts as a cofactor.

Test Kits and Assays

Relevant test kits are known in the art. The following are examples of test kits for evaluation against virus activity which can be used: WNV NS3 kit, HCV NS3 kit, and Thrombin Serin protease kit.

Also, whole cell assays can be carried out including, for example, whole cell HIV assays can be carried out.

Additional embodiments are provided by the following non-limiting working examples.

WORKING EXAMPLES

Part I

As part of a bioactives screening program from Red Sea invertebrates, the inventors detected a solid phase extract (SPE), achieved by fractioning a crude methanol extract using HP20SS bead and then desalting with water and eluting with 1:1 water/isopropanol, from the Red Sea sponge *Amphimedon chloros*, which showed antiviral activity against West Nile Virus NS3 protease.

The replicates of the "hit" SPE fraction were investigated by LC-MS and confirmed by GC-MS. The SPE fraction was further fractionated in order to isolate the prominent peaks identified by LC-MS using the technique of HPLC and determined retention times. The prominent peaks were collected and retested on the WNV NS3 protease kit (Anaspec) and the active fraction was identified.

LC-MS revealed that the composition of the active fraction consisted of 3 distinct compounds, which were further characterized via $MS^2$-assisted fragmentation of the compounds.

Compound 1:
ESI: m/z [M+H]+ 379.31 C26H39N2; $MS^2$: m/z [M+H]+ 190.159 C13H20N2

Compound 2:
ESI: m/z [M+H]+ 391.31 C27H39N2; $MS^2$: m/z [M+H]+ 202.159 C14H20N2, 190.159 C13H20N2

Compound 3:
ESI: m/z [M+H]+ 403.31 C28H39N2; $MS^2$: m/z [M+H]+ 379.310 C26H39N2

Compound 1, i.e. C26H39N2, is the dominant molecule in this fraction. $MS^2$ of the fraction reveals that compound is a symmetrical molecule consisting of two alkyl pyridines, with a six member pyridine ring attached to a carbon alkyl chain 9 (molecular weight of 189.159 Da, m/z [M+H]+ 190.159, FIG. 1). This is also observed in the GC-MS, as the parent compounds fragment predominantly to a pyridine-alkyl chain that has a 61.1% identity to the NIST database 4-undecyl pyridine (not shown). This molecule appears to be available in 2 states: cyclic and linear. Further testing was commenced on compound 1.

FIG. 1 shows mass spectral analysis: $MS^2$ of Compound 1 after fragmentation.

Figure 4:
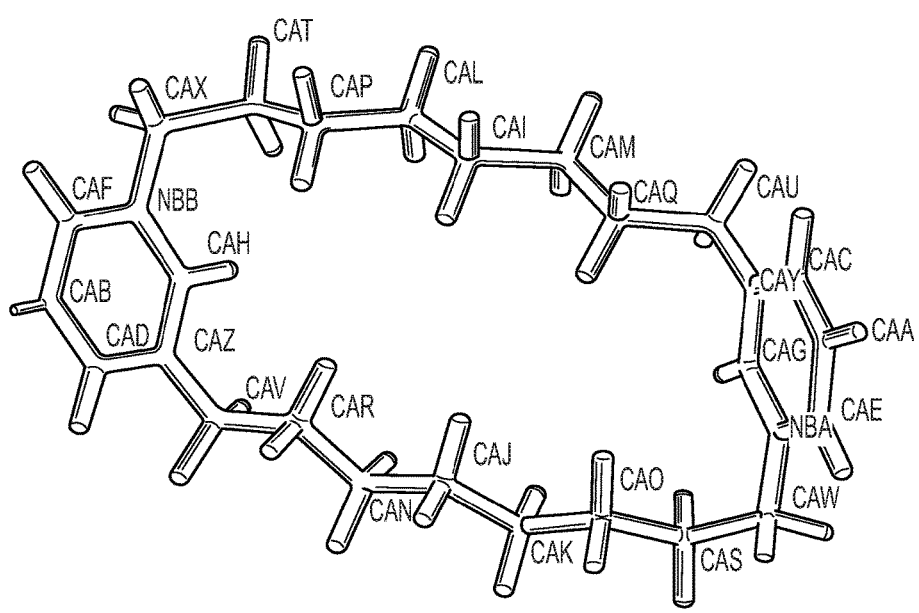
FIG. 4 shows a representation of compound 1 in a non-salt form.

FIG. 4 shows a representation of compound 1.

Activity Reports

Figure 2:
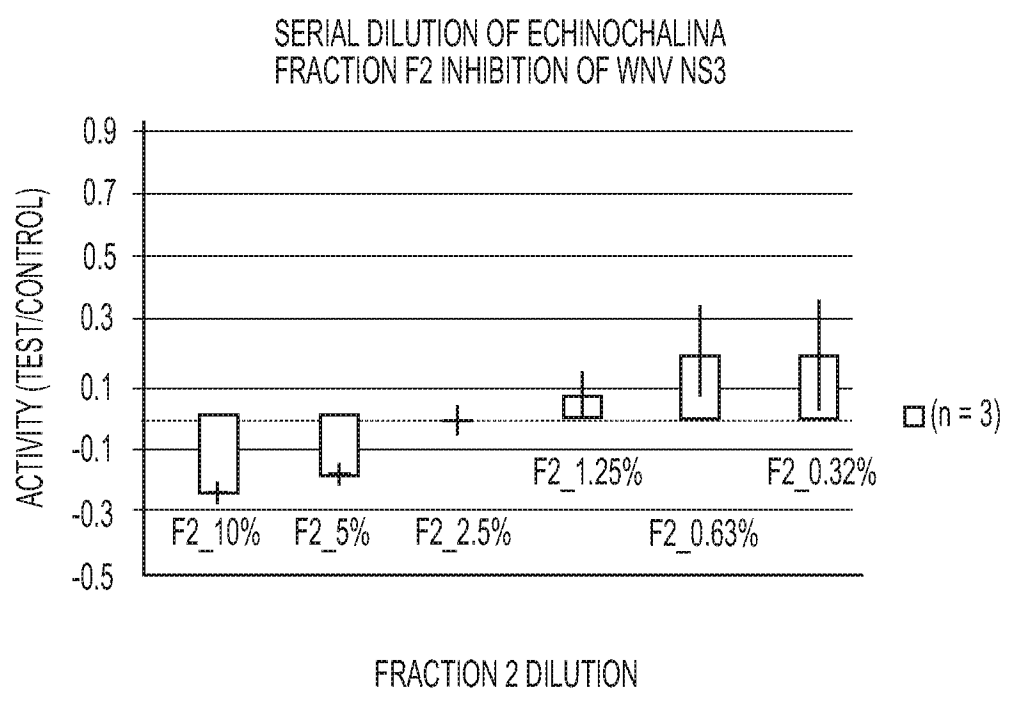

FIG. 2 shows an SPE activity report. The serial dilution of SPE fraction 2 from *C. viridis* (beginning at 10% methanol, n=3) shows strong inhibition of the in vitro WNV NS3 protease/substrate interaction. This gradually decreases at lower concentrations. Negative values suggest there is a threshold concentration for this assay.

Figure 3:
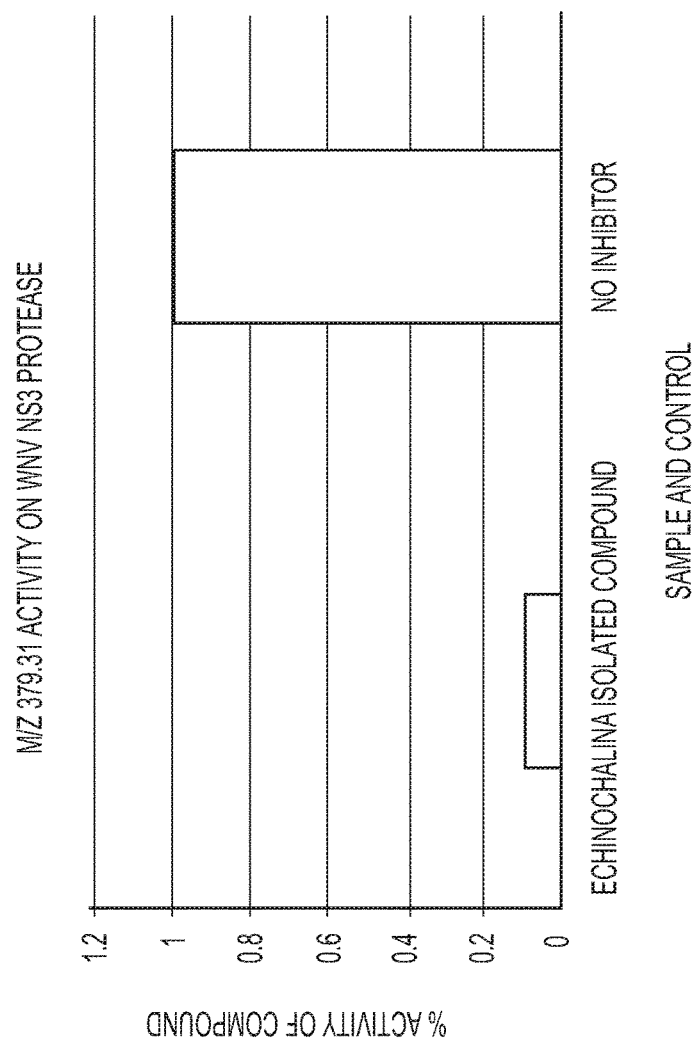
FIG. 3 shows Compound 1 activity.

FIG. 3 shows a Compound 1 activity report. The LC-MS characterized and HPLC isolated fraction which predominantly contains 379.31 (Compound 1) of the three molecules of interest is able to inhibit the activity of the NS3 protease up to 90%; whereas, the sample with no inhibitor allow for full activity of the protease.

(Part II) Additional Embodiments

Additional background and preferred embodiments, with working examples, are described hereinbelow and in the PhD thesis incorporated herein by reference: "Bioprospecting of Red Sea Sponges for Novel Anti-Viral Pharmacopoeias," Aubrie Elise O'Rourke, 2015, King Abdullah University of Science and Technology, Thuwal, Kingdom of Saudi Arabia; including Chapters 1 and 2 in particular.

A listing of cited references is also provided.

2.1 ABSTRACT 3-alkyl pyridinium compounds, commonly known as Halitoxins are a group of structurally diverse natural products and are commonly isolated from marine sponges. These molecules can be found as cyclic or linear compounds, as monomer or as polymer alkyl pyridiniums (poly-APS). They were first characterized in 1978 for their characteristic toxicity to fish and since then a number of of various biological activities have been identified. However, to date no conformation of a 3-alkyl pyridinium has been reported to show antiviral activity. The aim of this study was to assess the potential of a prefractionated organic extract of the Red Sea sponge *Amphimedon chloros* to inhibit the West Nile Virus NS3 protease (WNV NS3). The bioactive compound in the extract was determined using LC-MS and 1H and DOSY NMR. It was found that at 4.69 µg/ml the biological replicates of *A. chloros* show an inhibitory activity up to 60% upon the WNV NS3 protease in a biochemical assay. The activity elicited by the fraction is specific to the WNV NS3 protease and did not show inhibition of the HCV NS4A protease or Factor XA, a cellular serin protease. The compound was identified as a 3-alkyl pyridinium of Halitoxin by LC-MS and 1H NMR analysis. With the aid of DOSY NMR and an algorithm that relates the diffusion coefficient of the molecule to molecular weight, it was found the compound to be in the size range of 39 kDa. The same compound showed 60% cell loss when plated at 230 µg/ml on the human HeLa cell line. This study provides the first account of a Halitoxin exhibiting antiviral activity with negligible cytotoxicity.

2.2 INTRODUCTION

A well-represented group of marine natural products with unique structures are the Halitoxins. These 3-alkyl pyridinium molecules have acquired a number of hyponyms since the first isolation of the molecule, Halitoxin, from the sponge *Haliclona* sp. (1). The first compound from *Haliclona* was investigated for its characteristic ichthytoxocity. Accounts of the Halitoxin family bioactivity since the first isolation include epidermal growth factor (EGF) receptor activation (2), histone deacetylase inhibition (3), dorsal root ganglion (DRG) neuron activity (4), antifungal (5), antimycobacterial, and antimicrobial (6) activity as well as cytotoxicity (1, 7). The caveat to cytotoxicity is that 3-alkyl pyridiniums can be found as cyclic or linears compounds, as monomers or as polymer alkyl pyridiniums (poly-APS), where the cytotoxicity of the molecules is both size- and dose-dependent (8). Interestingly, macrocyclic compounds, in general, are noted for their flexibility, high potentency, selectivity, solubility, lipophilicity, membrane permeability, oral bioavailability, and metabolic stability and function as chemotherapeutics, immunosuppressants, antifungals, antiparasitics, antibacterials, and antivirals (9). However, it appears that to date no confirmation of a 3-alkyl pyridinium has been reported to show antiviral activity.

Many viruses have little representation in pharmacological screening efforts. One example is the West Nile Virus (WNV). The *Culex* mosquito transmits the virus, which manifests as the neglected tropical disease, West Nile Fever. Symptoms of the virus include: fever, headache, body aches, skin rash, swollen lymph glands and in extreme cases, encephalitis or meningitis. The virus is endemic mainly to Africa, the Middle East and around the Mediterranean Sea10 but remains a threat to other countries when the infected hosts, both mosquitoes and humans, travel. WNV is a flavivirus and in the Flaviviridae family with the Hepatitis C Virus (HCV). HCV currently has more than 34 prospective antivirals in various clinical phases whereas WNV has none.

The replication cycle of the WNV begins as the 45-50 nm enveloped, icoshedral nucleocapsid binds to unknown receptors on the host cell (PhD Thesis, Figure 2.1, step 1). Receptor mediated endocytosis brings the virion into the cell (PhD Thesis, Figure 2.1, step 2). The positive singlestranded 11 kb RNA genomes is uncoated (PhD thesis, Figure 2.1, Step 3) and can be directly translated by the host machinery into single long polyproteins at the rough endoplasmic reticulum (ER) (PhD thesis, Figure 2.1, Step 6). The polyprotein contains three structural proteins (capsid, premembrane, envelope) and seven non-structural (NS) proteins (NS1, NS2A, NS2B, NS3, NS4A, NS2B, NS5). The polyprotein must be cleaved by the NS3 protease in order to produce the individual proteins required for replication and particle maturation11 (PhD thesis, Figure 2.1, Step 7). The replication complex, which contains the NS5 RNA dependent RNA polymerase transcribes more viral RNA by generating a negative sense RNA strand to serve as a template for the polymerization of positive sense RNA (PhD thesis, Figure 2.1, Steps 4 and 5). A molecule that can inhibit the NS3 protease, will prohibit subsequent replication, packaging, and spread of the virus within the host organism. Viral proteases are good drug targets as exemplified by the nine clinically approved HIV protease inhibitors and two approved inhibitors of the HCV NS3 protease. As a result, the WNV NS3 protease is a promising target for screening efforts directed at inhibiting the West Nile Virus. The WNV NS3 protease is a serine protease with a marked homology to the four serotypes of Dengue Virus (DENV) NS3 protease, where all have been described to have an active site that is relatively flat and very exposed; two features that pose a problem for identifying inhibitors. As a result, the non-competitive binding site has also become a targeted domain. Ideally, an inhibitor that is effective at inhibiting the WNV may prove effective on the DENV.

In this study, a sponge-derived natural product library was screened and led to the identification of a fraction from the Red Sea sponge, *Amphimedon chloros*, which displays the ability to inhibit the WNV NS 3 protease in vitro. This activity is attributed to the 3-alkyl pyridiniums present in the fraction, which in their simplest form consist of an alkyl group connected to carbon three of a pyridine ring. An investigation into the Halitoxin or 3-alkylpyridinium class of compounds revealed a long-standing question of how to ascertain the relative size of these compounds. This question was addressed by employing the 2D NMR technique of DOSY. The technique in combination with an algorithm reported by Evans et al 2013 (12) provides a way to determine the molecular weight of a compound by its rate of diffusion. Knowing the molecular weight of the compound isolated from *A. chloros* allowed for the direct comparison of the cytotoxicity of the Halitoxin to cytotoxicity reports for other Halitoxins of various sizes. Provided here is the first account of antiviral activity for the Halitoxin family of compounds.

2.3 MATERIALS AND METHODS

2.3.1 *A. chloros* Sponge Collection

The *Amphimedon chloros* specimen were collected using gardening sheers from Inner Fsar reef (22°14'37.61"N; 39°00'28.03"E) off the coast of KAUST at 12 meters depth using SCUBA. The samples were briefly rinsed with 1% PBS, wrapped in foil and placed on ice, then frozen to −80° C. until processing. Dr. Nicole deVoogd provided assistance in the identification of *Amphimedon chloros* by spicule examination.

2.3.2 *A. chloros* Sponge Extraction 80 grams of sponge specimen were extracted with 1 liter of methanol then dried to 10 g of Diaion HP20SS beads then loaded into a column, desalted with deionized water (FW1, FW2) and then eluted in the following series: 25% IPA/$H_2O$, 50% IPA/$H_2O$, 75% IPA/$H_2O$, 100% MeOH (13).

2.3.3 West Nile Virus NS3 Protease Inhibition Assay

The West Nile Virus NS3 protease inhibition assay was carried out using the commercial kit SensoLyte® 440 West Nile Virus Protease Assay Kit (AnaSep, San Jose, Calif., USA). The protease is a truncated form of West Nile NS3 protease (residues 1-186) connected to it is NS2B cofactor (residues 49-96) by the linker sequence, GGGGSGGGG. Protease activity was assessed by its ability to cleave the fluorogenic peptide Pyr-RTKRAMC, and the subsequent production of free AMC (7-amino-4-methylcoumarin) fluorophores. All extracts and controls were performed with three replicates in a 384-well plate format, each with a total reaction mixture of 33 µl. To begin, the test extracts and protease solution were incubated at 37° C. for 10 min before the addition of the pre-heated substrate. After substrate addition and gentle mixing the reaction was incubated at 37° C. for one hour. The fluorophore was detected with the use of a SpectraMax® Paradigm® Multimode Microplate Detection Platform (Molecular Devices, Sunnyvale, Calif., USA) by scanning at 354 nm excitation wavelength and 442 n emission wavelength.

2.3.4 HCV NS3 Protease Inhibition Assay

The HCV NS3/4A protease inhibition assay was carried out using the commercial kit SensoLyte® 520 HCV Protease Assay Kit (AnaSep, San Jose, Calif., USA) [58]. The HCV NS3/4A protease is a 217 amino acid fusion protein (22.7 kDa) with NS4A co-factor fused to the Nterminus of NS3 protease domain. HCV NS3/4A protease activity was assessed by its ability to cleave the fluorogenic FRET peptide, and the subsequent unquenching by QXL 520 quencher of the 5-FAM fluorophore, which emits fluorescence. All extracts and controls were performed with three replicates in a 384-well plate format, each with a total reaction mixture of 18 µL. To begin, the test extracts and protease solution were incubated at room temperature for 10 min before the addition of the substrate. After substrate addition and gentle mixing the reaction was incubated at room temperature for one hour. The fluorophore was detected with the use of a SpectraMax® Paradigm® Multi-mode Microplate Detection Platform (Molecular Devices, Sunnyvale, Calif., USA) by scanning at 490 nm excitation wavelength and 520 nm emission wavelength.

2.3.5 Thrombin Serine Protease Inhibition Assay

The Factor Xa/Thrombin inhibition assay was carried out using the commercial kit SensoLyte® 520 Factor Xa Assay Kit (AnaSep, San Jose, Calif., USA). Thrombin Xa activity was assessed by its ability to cleave the fluorogenic FRET peptide, and the subsequent unquenching by QXL 520 quencher of the 5-FAM fluorophore which emits fluorescence. All extracts and controls were performed with three replicates in a 384-well plate format, each with a total reaction mixture of 12.5 µL. To begin, the test extracts and Thrombin/Factor Xa solution were incubated for five minutes then the substrate was added. After substrate addition and gentle mixing the reaction was incubated at room temperature for one hour. The fluorophore was detected with the use of a SpectraMax® Paradigm® Multi-mode Microplate Detection Platform (Molecular Devices, Sunnyvale, Calif., USA) by scanning at 490 nm excitation wavelength and 520 nm emission wavelength.

2.3.6 Cytotoxicity/HCA of *A. chloros*

A serial dilution of *A. chloros* SPE fraction 2 (230 µg/ml, 115 µg/ml and 57.5 µg/ml) was plated on HeLa cells cultured and stained in the same fashion as reported in Chapter 1 of the O'Rourke PhD thesis incorporated herein by reference.

2.3.7 LC-MS of *A. chloros* Bioactive Compound

Liquid chromatography-mass spectrometry (LC-MS) was carried out on the Thermo LTQ Orbitrap instrument in positive mode using electrospray ionization. The 10 µl of solid phase extracted (SPE) sponge material was separated using a ZORBAX Eclipse XDB-C18 LC Column, 4.6 mm, 150 mm, 5 µm and the gradient displayed in Table 1.

TABLE 1

HPLC gradient used to separate the *A. chloros* SPE fraction 2.

| Time | % H20 | % MeOH | Formic acid in each solvent |
|---|---|---|---|
| 0 min | 90 | 10 | 0.10% |
| 5 min | 90 | 10 | 0.10% |
| 40 min | 10 | 90 | 0.10% |
| 50 min | 10 | 90 | 0.10% |
| 55 min | 90 | 10 | 0.10% |
| 60 min | 90 | 10 | 0.10% |

2.3.8 NMR of *A. chloros* 3-alkyl Pyridinium 12 mg of the isolated 3-alkyl pyridinium compound was evaluated using 1H and 2 D DOSY on a Bruker 600 MHz with a 5 mm NMR Economy Sample Tube (Wilmad-LabGlass). The DOSY experimental data was obtained using double stimulated echo gradient pulse pair and three spoil gradients pulse sequences (dstegp3s) in the standard Bruker pulse sequence library. The gradient shape was sinusoidal and its length (δ) was optimized at 2.3 ms; its strength increased linearly, acquiring 32 steps of gradient levels. A gradient recovery delay of 1.5 ms was used and the diffusion time (Δ) values was set to 300 ms (D20 of 300 ms and a P30 of 2400 µs at 298K.). Low and high gradient strengths were set at 5 and 95% of maximum, respectively. Each spectrum was recorded by collecting 128 transients with 10 second recycle delay. The experiment was run with CD2OD as the solvent for 16 hrs, ns=128 for each of the 32 ramp cycles.

2.4 RESULTS

2.4.1 A. chloros Demonstrates Inhibition of West Nile Virus NS3 Protease

Biological replicates of *A. chloros* SPE-fractionated organic extracts screened for activity against WNV NS3 protease revealed fraction 2 for all replicates (s36F2, c16F2, c23F2) to show a strong inhibition of NS3 activity at 37.5 µg/ml (FIG. 5A). Serial dilutions of the biological replicates of fraction 2 were performed showing a strong inhibition of NS3 protease activity to the lowest concentration of 4.69 µg/ml with more than 60% inhibition (FIG. 5B). The same set of samples were screened for their ability to inhibit the HCV protease as well as Factor Xa associated with the serine protease, thrombin. All samples failed to show inhibition of either target.

2.4.2 High-Content Screening Reveals Cytotoxic of A. chloros Treatment

Figure 6:
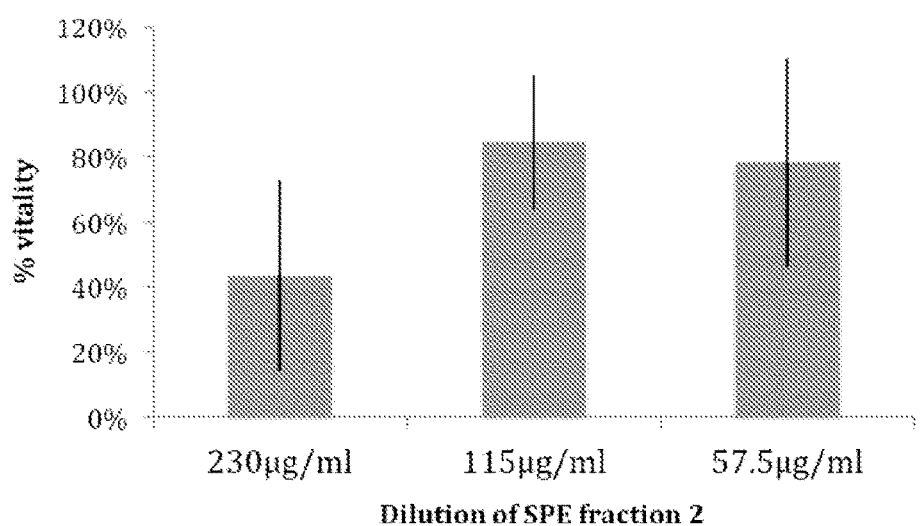

With hierarchical clustering using Spearman distance and complete linkage, it was shown in the incorporated PhD thesis, Chapter 1, that all biological replicates of *Amphimedon chloros* fraction 2 cluster with the LOPAC compounds CBIQ, Corticosterone and more distantly to Gossypol, Quazinone, Quercetin dehydrate and TG003. These compounds were tested on the WNV assay and showed no inhibition of the WNV NS protease. Cell counts of the HeLa cells cultures treated with the sponge test compounds show that the first dilution (230 µg/ml) used for generating HCA heatmap in Chapter 1 results in 60% cell loss. The following serial dilutions (115 µg/ml and 57.5 µg/ml) approach 100% vitality (FIG. 6). This can be compared to the 37.5 µg/ml used in the WNV screen and shows us this concentration is expected to have cell vitality around 80%.

2.4.3 Analytical Chemistry Reveals 3-alkyl Pyridinium as Bioactive Compound

The MS2 spectrum of the active SPE fraction 2 shows an abundance of a symmetrical compound with m/z 379.31 [M+H]+, composed for two smaller components at m/z 190 [M+H]+ (FIG. 7). The 1H NMR reported in the Supplemental material of Davies-Coleman and the present 1H spectra present the same signals. Their findings and ours, reported in brackets, are as follows: delta 8.95 [9.00], 8.84 [8.91], 8.45 [8.45], 8.01 [8.07] that are attributed to the 3-substituted pyridinium salt; delta at 4.60 [4.66] attributed to the methylene group on the quaternary nitrogen, which is coupled to a methylene signal at 2.20 [2.21], further coupled to a methylene envelope at delta 1.41 [1.41]; and a signal at delta 2.87 [2.87] assigned to the methylene group to the C-3 position of the pyridinium ring, coupled to a methylene signal at delta 1.73 [1.73]. Also observed was the presence of a peak at 1.31 in both spectra, but with great intensity in our sample, which we assume is associated with the methylene envelope at delta 1.41. A solvent phase shift was observed for the deuterated methanol—d4 at 3.31 ppm and 4.87 ppm as expected (FIG. 7).

2.4.4 DOSY Reveals the Approximate size of the 3-alkyl Pyridinium Bioactive Compound Recently, DOSY experimentation has been used to analyze mixtures of small to medium-sized molecules in order to determine the molecular weights of unknowns. Evans et al. (12) took the approach one step further, keeping in mind that not all compounds are spheres moving through a continuum fluid. They were able to derive an expression to relate the diffusion coefficient to the molecular weight for a wide range of small molecules in a range of solvents. Their equation provides simplicity with a root mean square difference between experimental and estimated diffusion coefficients of only 15%. The 2D DOSY diffusion variable gradient was calculated for the most intense peak at delta 1.31, which is attributed to the methylene envelope of the halitoxin compound.

From this, the diffusion coefficient (D) of 1.34 E-10m2/s was acquired, and using the algorithm from Evans et al., the molecular weight was estimated at approximately 39 kDa for the halitoxin compound from its DOSY calculated rate of diffusion (Figure 2.6).

2.5 MORE BACKGROUND AND DISCUSSION

Since the isolation of the first Halitoxin, a total of approximately 67 examples of 3-alkyl pyridium compounds have been reported from the species *Haliclona* (14) as well as from other sponge genera, including, *Theonella* (15), *Amphimedon* (16), *Callyspongia* (2), *Cribochalina* (5), (17), *Echinochalina* (18), *Pachychalina* (19), *Niphates* (20), and *Reniera* (21). Only one example has been isolated from a source outside of Porifera; this is from the mollusk *Haminoea orbignyana* (22).

3-alkyl pyridiniums in their simplest form consist of an alkyl group connected to carbon three of a pyridine ring. Halitoxins can be found as monomers with different alkyl chain lengths or as polymers of alkyl pyridiniums (poly-APS) connected in a head-to-tail or tail-to-tail arrangement or in a cyclic motif where the free tail of the alkyl chain connects to the nitrogen of another pyridine ring. The original compound, Halitoxin, was in essence a poly-APS, isolated on account of its toxicity to fish. Polymers in the size range of 500-1000 Daltons as well as the broad range from 1-25 kDa were found to have an ED50 of 5-7 µg/ml when tested on the KB line of cancer cells—all compound with masses less than 500 Daltons were excluded and reported to be nontoxic (1). Poly-APS are also known for their ability to act as surfactants and for their antifouling, antifungal and anti-algal activity. The cyclic variety of 3-alkyl pyridiniums are reported to have various bioactivies, such as the ability to inhibit histone deacetylase (3), activate epidermal growth factor (EGF) activity (2) and a exhibit a depolarizing effect on dorsal root ganglion (DRG) neurons (4), anticholinesterase (23) as well as harboring antimicrobial and antimycobacterial (24) activity.

Various sizes of Poly-APS compounds have been evaluated for their ability to form pores in membranes, overall effect of cytotoxicity, and the ability of the cell to recover after exposure. As a result, their value as facilitators of drug delivery has been suggested, and a dose-dependence was found where an amount of less than 5.0 µg/ml allowed for recoverability of the cell without cytotoxicity for high molecular weight compounds between 5.5 and 19 kDa (8). It follows that the cytotoxicity of the compound may correlate to the size of the compound and the given dosage.

The fractionation used in the study presented here is the same solid phase extraction protocol presented in Bugni, Harper, McCulloch, Reppart and Ireland (13), where the crude extract of *Pseudoceratina purpurea* was dried onto Diaion HP20SS beads in order to fractionate the sample, similarly, they found a molecule at m/z 379.3123 (calcd for C26H39N2, 379.3113) and m/z 190.1585 (calcd for C13H20N, 190.1596) that showed activity in a luciferase assay, and corresponds to our compound and its fragment. The compound was dismissed as a common hit in high throughput screening and the project was dropped on account of its classification as a Halitoxin, as class of compounds known for cytotoxicity.

Figure 7A:
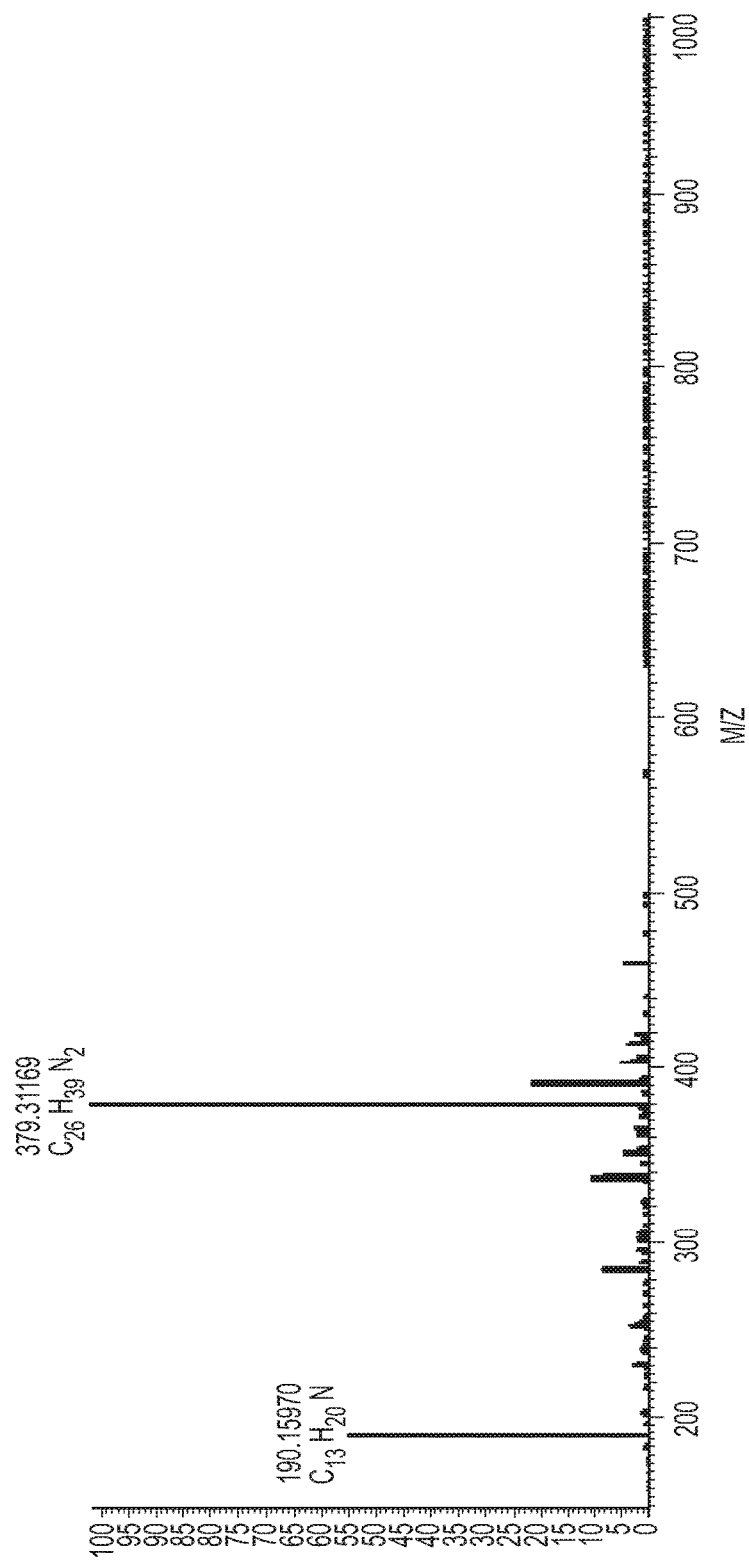
Figure 7B:
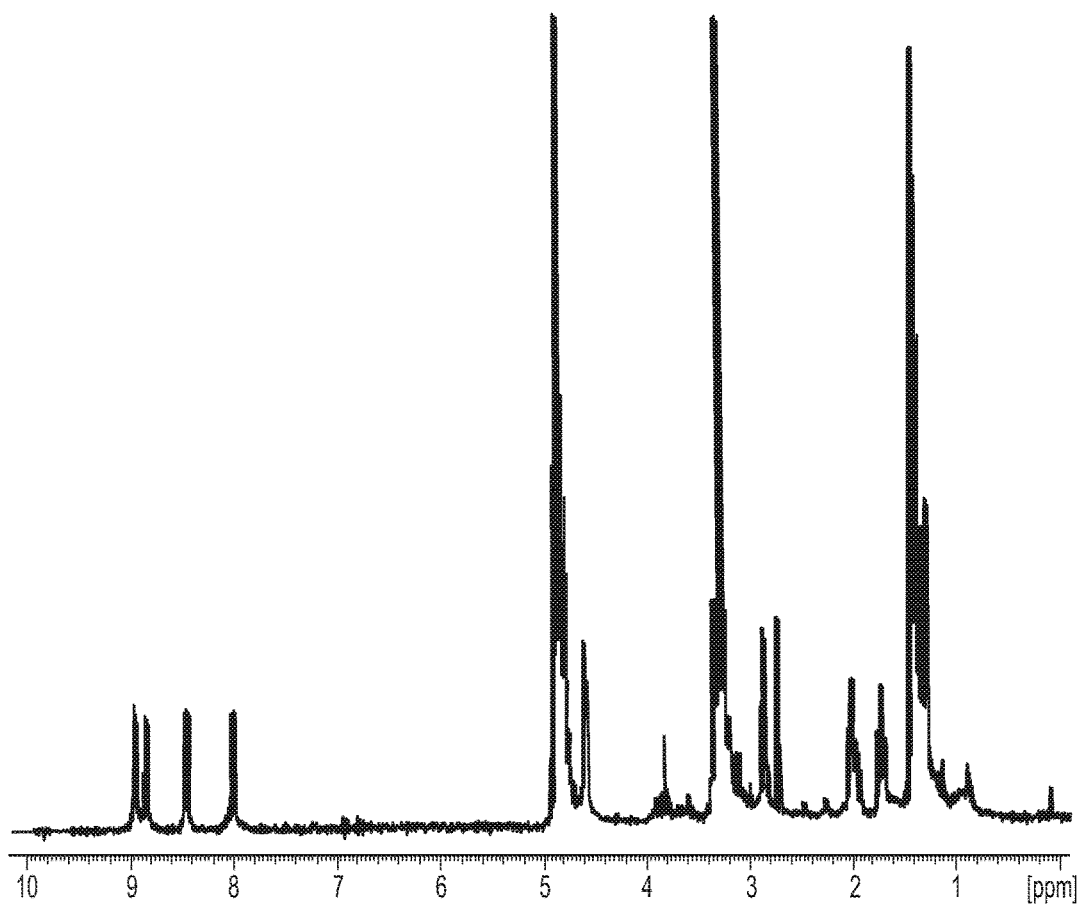
Figure 7C:
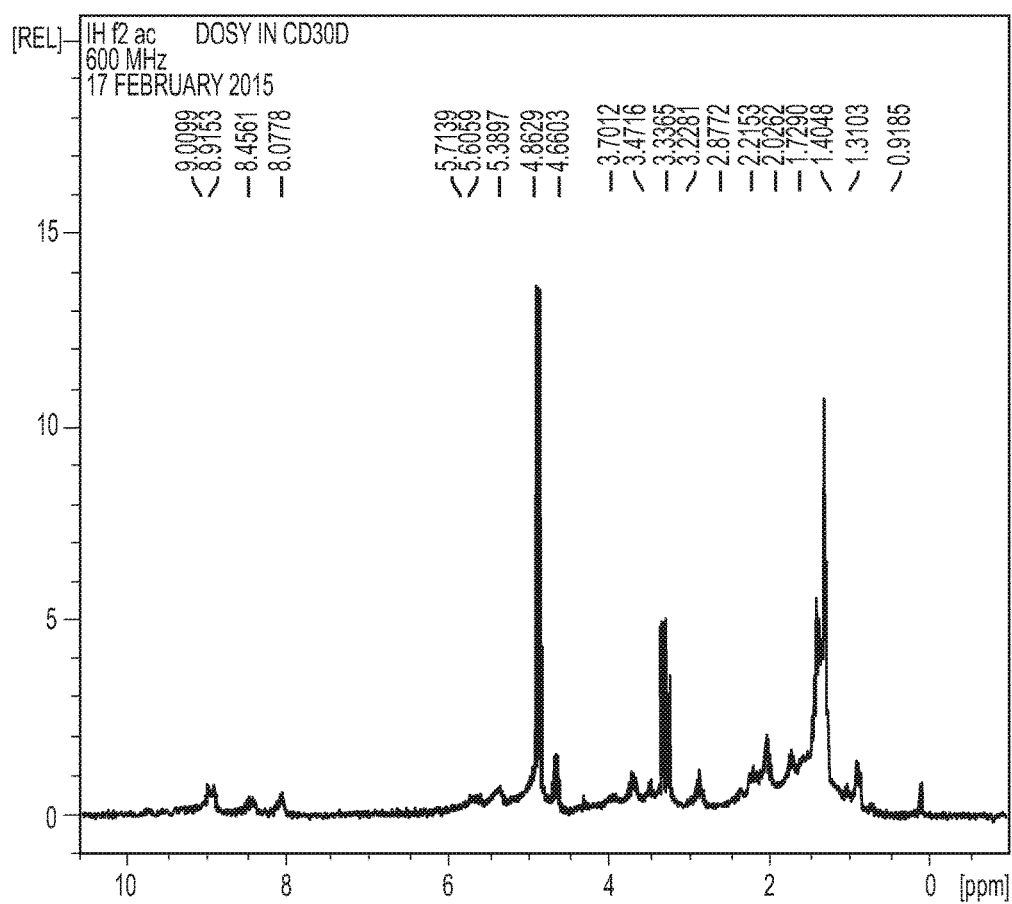
Figure 7D:
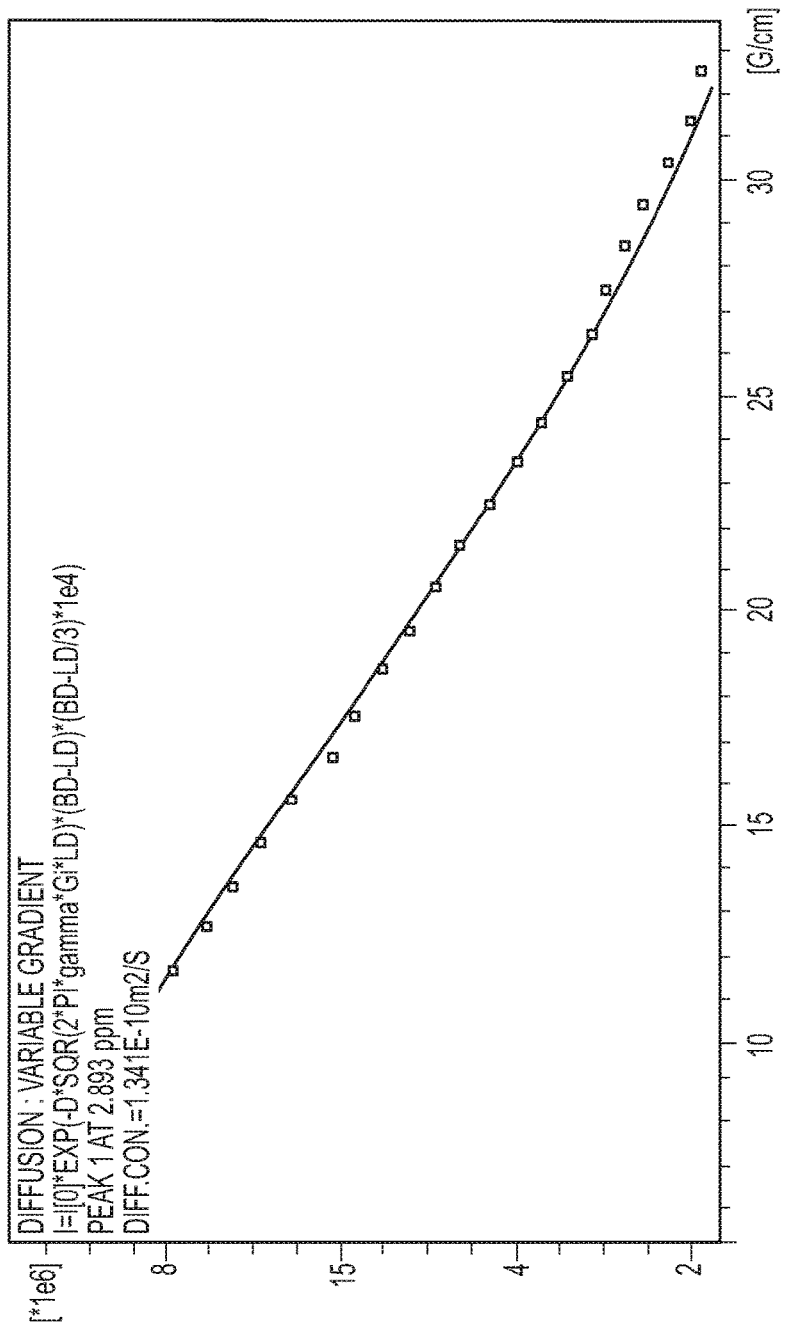

The first characterization of this class of compounds was from a compound isolated from the sponge, *Callyspongia fibrosa*, by Davies-Coleman (2) in 1993. They report this compound to cause an activation of EGFR. The 3-alkyl pyridinium, which was identified from the Red Sea sponge *Amphimedon chloros*, appears to be the same compound as the one described in the study of 1992. This is because their LC-MS experimentation report similar peaks at m/z 379 as well as the m/z 190.1585 as was found in the present experimentation (FIG. 7A). Furthermore, the 1H NMR reported in the supplemental material of Davies-Coleman and 1H spectra presented here mirror the same signals (FIG. 4B, C). Their findings and findings from this study, reported in brackets, are as follows: delta 8.95 [9.00], 8.84 [8.91], 8.45 [8.45], 8.01 [8.07] that are attributed to the 3-substituted pyridinium salt; delta at 4.60 [4.66] attributed to the methylene group on the quaternary nitrogen, which as coupled to a methylene signal at 2.20 [2.21], further coupled to a methylene envelope at delta 1.41 [1.40]; and a signal at delta 2.87 [2.87] assigned to the methylene group bound to the C-3 position of the pyridinium ring, coupled to a methylene signal at delta 1.73 [1.73]. The present study also observed the presence of a peak at delta 1.31 in both spectra, but with greater intensity in our sample, which it is assumed is also associated with a resonance of the broad methylene envelope at delta 1.41.

In Davies-Coleman et al. 1993 (2) the authors attempted to synthesize the compound that they proposed. However, they were unable to generate the symmetrical cyclic compound with an m/z of 379, composed of two 3-alkyl pyridinium monomers at m/z 190.15. This led them to conclude that the compound they had isolated was giving an LC-MS fragmentation confounded by the ionization method and further concluded that their compound could be the fragment of a larger molecule. This issue reoccurred in other reports of the Halitoxins where activity was found but the absolute molecular size was unclear. It is certain that Halitoxins come in a variety of sizes from 500 Da to 25 kDa and as displayed in previous literature, Halitoxin cytotoxicity is dose-dependent and size dependent. The task then becomes accurately reporting on the size of the Halitoxin in order to assess its dosage.

In order to answer this question the 2D NMR technique of DOSY was used. This experiment evaluates the diffusion of purified samples as well as mixtures. It operates on the principle that molecules in liquids move and this translational motion is known as diffusion Recently, DOSY experimentation has been used to analyze mixtures of small to medium sized molecules in order to determine the molecular weights of unknowns. Evans et al. 2013 (12), derived an expression to relate the diffusion coefficient to the molecular weight for a wide range of small molecules in a range of solvents. Using the DOSY technique and the algorithm from Evans et al. 2013 12, a diffusion coefficient of 1.34 E-10m2/s allowed for the molecular weight estimate of approximately 39 kDa for the bioactive Halitoxin (FIG. 4D). This suggests that the LC-MS spectra that was presently found and what was reported by Davies-Coleman showing only a fragment of the larger poly-APS compound—a compound 200 times larger than the 3-alkyl pyridinium monomer of m/z 190.15 and 100 times larger than the m/z 379 fragment.

From previous accounts of cytotoxicity for compounds in the broad size range of 0.5-25 kDa with a reported ED50 of 5-7 µg/ml on the KB line of cancer cells, as well as accounts of cell recoverability after a 5 µg/ml treatment with high molecular weight compounds between 5.5 and 19 kDa, the assessment can be made that the potency of our compound as an inhibitor of the WNV NS3 protease is not offset by an in vivo cytotoxicity.

It was demonstrated that the presently isolated compound has an inhibitory activity up to 60% upon the WNV NS3 protease at 4.69 µg/ml (FIG. 5B). This inhibition is specific to the WNV NS3 protease as demonstrated by the lack of inhibitory activity of the fraction when tested on the thrombin and HCV serine proteases. The alkyl pyridinium fraction when plated on HeLa cells at 230 µg/ml showed 50% cell loss (FIG. 6). When manifestations of toxicity do arise, they are observed to adversely affect the actin and tubulin, the mitochondria and the ER, as well as the ability to cause a down-regulation of the cell-cycle associated protein NFkB in HeLa cells. As a result of the present experimentation, it was proposed that the poly-APS that has been characterized as approximately 39 kDa, is a large Halitoxin, and the concentration at which inhibition is observed is low enough to avoid cytotoxicity to the host cell.

2.7 REFERENCES

1. Schmitz, F. J.; Hollenbeak, K. H.; Campbell, D. C., Marine Natural-Products—Halitoxin, Toxic Complex of Several Marine Sponges of Genus *Haliclona*. *Journal of Organic Chemistry* 1978, 43 (20), 3916-3922.
2. Daviescoleman, M. T.; Faulkner, D. J.; Dubowchik, G. M.; Roth, G. P.; Polson, C.; Fairchild, C., A New Egf-Active Polymeric Pyridinium Alkaloid from the Sponge *Callyspongia-Fibrosa*. *Journal of Organic Chemistry* 1993, 58 (22), 5925-5930.
3. Oku, N.; Nagai, K.; Shindoh, N.; Terada, Y.; van Soest, R. W. M.; Matsunaga, S.; Fusetani, N., Three new cyclostellettamines, which inhibit histone deacetylase, from a marine sponge of the genus *Xestospongia*. *Bioorganic & medicinal chemistry letters* 2004, 14 (10), 2617-2620.
4. Scott, R. H.; Whyment, A. D.; Foster, A.; Gordon, K. H.; Milne, B. F.; Jaspars, M., Analysis of the structure and electrophysiological actions of halitoxins: 1,3 alkyl-pyridinium salts from *Callyspongia ridleyi*. *Journal of Membrane Biology* 2000, 176 (2), 119-131.
5. Matsunaga, S.; Shinoda, K.; Fusetani, N., Bioactive Marine Metabolites. Cribrochalinamine Oxide-a and Oxide-B, Antifungal Beta-Substituted Pyridines with an Azomethine N-Oxide from a Marine Sponge *Cribrochalina* Sp. *Tetrahedron Lett* 1993, 34 (37), 5953-5954.
6. de Oliveira, J. H. H. L.; Seleghim, M. H. R.; Timm, C.; Grube, A.; Kock, M.; Nascimento, G. G. F.; Martins, A. C. T.; Silva, E. G. O.; de Souza, A. O.; Minarini, P. R. R.; Galetti, F. C. S.; Silva, C. L.; Hajdu, E.; Berlinck, R. G. S., Antimicrobial and antimycobacterial activity of cyclostellettamine alkaloids from sponge *Pachychalina* sp. *Marine Drugs* 2006, 4 (1), 1-8.
7. Dasari, V. R. R. K.; Muthyala, M. K. K.; Nikku, M. Y.; Donthireddy, R. R., Novel Pyridinium compound from marine actinomycete, *Amycolatopsis alba* var. nov DVR D4 showing antimicrobial and cytotoxic activities in vitro. *Microbiological Research* 2012, 167 (6), 346-351.
8. Tucker, S. J.; McClelland, D.; Jaspars, M.; Sepcic, K.; MacEwan, D. J.; Scott, R. H., The influence of alkyl pyridinium sponge toxins on membrane properties, cytotoxicity, transfection and protein expression in mammalian cells. *Biochimica Et Biophysica Acta-Biomembranes* 2003, 1614 (2), 171-181.
9. Yu, X.; Sun, D., Macrocyclic drugs and synthetic methodologies toward macrocycles. *Molecules* 2013, 18 (6), 6230-68.

10. Leyssen, P.; De Clercq, E.; Neyts, J., Perspectives for the treatment of infections with Flaviviridae. *Clinical microbiology reviews* 2000, 13 (1), 67-82, table of contents.
11. Cregar-Hernandez, L.; Jiao, G. S.; Johnson, A. T.; Lehrer, A. T.; Wong, T. A.; Margosiak, S. A., Small molecule pan-dengue and West Nile virus NS3 protease inhibitors. *Antivir Chem Chemother* 2011, 21 (5), 209-17.
12. Evans, R.; Deng, Z.; Rogerson, A. K.; McLachlan, A. S.; Richards, J. J.; Nilsson, M.; Morris, G. A., Quantitative interpretation of diffusion-ordered NMR spectra: can we rationalize small molecule diffusion coefficients? *Angew Chem Int Ed Engl* 2013, 52 (11), 3199-202.
13. Bugni, T. S.; Harper, M. K.; McCulloch, M. W. B.; Reppart, J.; Ireland, C. M., Fractionated marine invertebrate extract libraries for drug discovery. *Molecules* 2008, 13 (6), 1372-1383.
14. (a) Volk, C. A.; Kock, M., Viscosaline: new 3-alkyl pyridinium alkaloid from the Arctic sponge *Haliclona viscosa*. *Org Biomol Chem* 2004, 2 (13), 1827-1830; (b) Teruya, T.; Kobayashi, K.; Suenaga, K.; Kigoshi, H., Cyclohaliclonamines A-E: Dimeric, trimeric, tetrameric, pentameric, and hexameric 3-alkyl pyridinium alkaloids from a marine sponge *Haliclona* sp. *Journal of natural products* 2006, 69 (1), 135-137.
15. Kobayashi, J.; Murayama, T.; Ohizumi, Y., Theonelladins-a-D, Novel Antineoplastic Pyridine Alkaloids from the Okinawan Marine Sponge *Theonella-Swinhoei*. *Tetrahedron Letters* 1989, 30 (36), 4833-4836.
16. (a) Albrizio, S.; Ciminiello, P.; Fattorusso, E.; Magno, S.; Pawlik, J. R., Amphitoxin, a New High-Molecular-Weight Antifeedant Pyridinium Salt from the Caribbean Sponge *Amphimedon Compressa*. *Journal of Natural Products-Lloydia* 1995, 58 (5), 647-652; (b) Tsuda, M.; Hirano, K.; Kubota, T.; Kobayashi, J., Pyrinodemin A, a cytotoxic pyridine alkaloid with an isoxazolidine moiety from sponge *Amphimedon* sp. *Tetrahedron Letters* 1999, 40 (26), 4819-4820; (c) Hirano, K.; Kubota, T.; Tsuda, M.; Mikami, Y.; Kobayashi, J., Pyrinodemins B-D, potent cytotoxic bis-pyridine alkaloids from marine sponge *Amphimedon* sp. *Chemical & Pharmaceutical Bulletin* 2000, 48 (7), 974-977.
17. Kariya, Y.; Kubota, T.; Fromont, J.; Kobayashi, J., Pyrinadine A, a novel pyridine alkaloid with an azoxy moiety from sponge *Cribrochalina* sp. *Tetrahedron Letters* 2006, 47 (6), 997-998.
18. Jimenez, J. I.; Goetz, G.; Mau, C. M. S.; Yoshida, W. Y.; Scheuer, P. J.; Williamson, R. T.; Kelly, M., 'Upenamide: An unprecedented macrocyclic alkaloid from the Indonesian sponge *Echinochalina* sp. *Journal of Organic Chemistry* 2000, 65 (25), 8465-8469.
19. (a) de Oliveira, J. H.; Grube, A.; Kock, M.; Berlinck, R. G.; Macedo, M. L.; Ferreira, A. G.; Hajdu, E., Ingenamine G and cyclostellettamines G-I, K, and L from the new Brazilian species of marine sponge *Pachychalina* sp. *J Nat Prod* 2004, 67 (10), 1685-9; (b) Laville, R.; Thomas, O. P.; Berrue, F.; Reyes, F.; Amade, P., Pachychalines A-C: Novel 3-alkylpyridinium salts from the marine sponge *Pachychalina* sp. *Eur J Org Chem* 2008, (1), 121-125.
20. (a) Krauss, J.; Wetzel, I.; Bracher, F., A new approach towards ikimine A analogues. *Natural Product Research* 2004, 18 (5), 397-401; (b) Kobayashi, J.; Murayama, T.; Kosuge, S.; Kanda, F.; Ishibashi, M.; Kobayashi, H.; Ohizumi, Y.; Ohta, T.; Nozoe, S.; Sasaki, T., Niphatesines a-D, New Antineoplastic Pyridine Alkaloids from the Okinawan Marine Sponge *Niphates* Sp. *Journal of the Chemical Society-Perkin Transactions* 1 1990, (12), 3301-3303; (c) Kobayashi, J.; Zeng, C. M.; Ishibashi, M.; Shigemori, H.; Sasaki, T.; Mikami, Y., Niphatesines E-H, New Pyridine Alkaloids from the Okinawan Marine Sponge *Niphates* Sp. *Journal of the Chemical Society-Perkin Transactions* 1 1992, (11), 1291-1294.
21. Laville, R.; Genta-Jouve, G.; Urda, C.; Fernandez, R.; Thomas, O. P.; Reyes, F.; Amade, P., Njaoaminiums A, B, and C: Cyclic 3-Alkylpyridinium Salts from the Marine Sponge *Reniera* sp. *Molecules* 2009, 14 (11), 4716-4724.
22. Cutignano, A.; Cimino, G.; Giordano, A.; D'Ippolito, G.; Fontana, A., Polyketide origin of 3-alkylpyridines in the marine mollusc *Haminoea orbignyana*. *Tetrahedron Lett* 2004, 45 (12), 2627-2629.
23. Sepcic, K.; Batista, U.; Vacelet, J.; Macek, P.; Turk, T., Biological activities of aqueous extracts from marine sponges and cytotoxic effects of 3-alkylpyridinium polymers from *Reniera sarai*. *Comp Biochem Physiol C Pharmacol Toxicol Endocrinol* 1997, 117 (1), 47-53.
24. Arai, M.; Ishida, S.; Setiawan, A.; Kobayashi, M., aliclonacyclamines, tetracyclic alkylpiperidine alkaloids, as anti-dormant mycobacterial substances from a marine sponge of *Haliclona* sp. *Chem Pharm Bull (Tokyo)* 2009, 57 (10), 1136-8.
25. Kobayashi, J.; Tsuda, M.; Kawasaki, N.; Matsumoto, K.; Adachi, T., Keramaphidin-B, a Novel Pentacyclic Alkaloid from a Marine Sponge *Amphimedon* Sp—a Plausible Biogenetic Precursor of Manzamine Alkaloids. *Tetrahedron Lett* 1994, 35 (25), 4383-4386.
26. Kura, K.; Kubota, T.; Fromont, J.; Kobayashi, J., Pyrinodemins E and F, new 3-alkylpyridine alkaloids from sponge *Amphimedon* sp. *Bioorganic & medicinal chemistry letters* 2011, 21 (1), 267-70.
27. Defant, A.; Mancini, I.; Raspor, L.; Guella, G.; Turk, T.; Sepcic, K., New Structural Insights into Saraines A, B, and C, Macrocyclic Alkaloids from the Mediterranean Sponge *Reniera (Haliclona) sarai*. *Eur J Org Chem* 2011, (20-21), 3761-3767.
28. Tiraboschi, P.; Chito, E.; Sacco, L.; Sala, M.; Stefanini, S.; Defanti, C. A., Evaluating voting competence in persons with Alzheimer disease. *International journal of Alzheimer's disease* 2011, 2011, 983895.
29. Arai, M.; Ishida, S.; Settawan, A.; Kobayashi, M., Haliclonacyclamines, Tetracyclic Alkylpiperidine Alkaloids, as Anti-dormant Mycobacterial Substances from a Marine Sponge of *Haliclona* sp. *Chem Pharm Bull* 2009, 57 (10), 1136-1138.
30. Damodaran, V.; Ryan, J. L.; Keyzers, R. A., Cyclic 3-alkyl pyridinium alkaloid monomers from a New Zealand *Haliclona* sp. marine sponge. *J Nat Prod* 2013, 76 (10), 1997-2001.

What is claimed is:

1. A method for treating a viral infection in a patient in need thereof, comprising administering to the patient a therapeutically effective amount of a compound, or a pharmaceutically acceptable salt thereof, wherein the compound comprises at least one alkyl pyridinium compound represented by Formula (3):

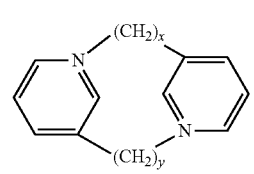

Formula (3)

wherein x and y, independently of each other, are each 5-15.

2. The method of claim 1, wherein the compound, or pharmaceutically acceptable salt, has a number average molecular weight of 30,000 daltons to 50,000 daltons.

3. The method of claim 1, wherein the therapeutically effective amount of the compound or pharmaceutically acceptable salt thereof is provided in the form of a solid having an amount of at least 1 wt. % of the compound or pharmaceutically acceptable salt thereof.

4. The method of claim 1, wherein the patient is infected with a retrovirus.

5. The method of claim 1, wherein the patient is infected with a lentivirus.

6. The method of claim 1, wherein the patient is infected with an HIV virus.

7. The method of claim 1, wherein the therapeutically effective amount is provided in the form of a solid having an amount of active ingredient of at least 5 wt. %.

8. The method of claim 1, wherein the compound is represented by Formula (4):

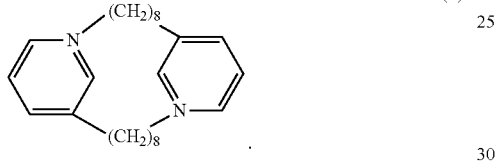

Formula (4)

* * * * *